United States Patent
Newman et al.

(10) Patent No.: US 11,431,796 B1
(45) Date of Patent: *Aug. 30, 2022

(54) WEB AND MOBILE-BASED PLATFORM THAT UNITES WORKFLOW MANAGEMENT AND ASYNCHRONOUS VIDEO COLLABORATION FOR HEALTHCARE

(71) Applicant: Vii Network, Inc., Washington, DC (US)

(72) Inventors: Phil Newman, Washington, DC (US); Steve Grimm, Silver Spring, MD (US); Paul Winterling, Baltimore, MD (US)

(73) Assignee: Vii Network, Inc., Washington, DC (US)

( * ) Notice: Subject to any disclaimer, the term of this patent is extended or adjusted under 35 U.S.C. 154(b) by 694 days.

This patent is subject to a terminal disclaimer.

(21) Appl. No.: 16/393,520

(22) Filed: Apr. 24, 2019

Related U.S. Application Data

(63) Continuation of application No. 14/484,912, filed on Sep. 12, 2014, now Pat. No. 10,320,903.
(Continued)

(51) Int. Cl.
*H04L 67/00* (2022.01)
*H04L 67/1095* (2022.01)
(Continued)

(52) U.S. Cl.
CPC ........ *H04L 67/1095* (2013.01); *G06F 16/273* (2019.01); *G06Q 10/101* (2013.01);
(Continued)

(58) Field of Classification Search
None
See application file for complete search history.

(56) References Cited

U.S. PATENT DOCUMENTS

| 6,195,368 B1 | 2/2001 | Gratacap |
| 6,263,362 B1 * | 7/2001 | Donoho ................. H04L 67/53 709/225 |

(Continued)

FOREIGN PATENT DOCUMENTS

| JP | 09294784 | 11/1997 |
| KR | 20110134737 A | 12/2011 |
| WO | 2010087795 A1 | 8/2010 |

OTHER PUBLICATIONS

International Search Report and Written Opinion dated Dec. 23, 2014 for PCT/US2014/055413.

*Primary Examiner* — Farhan M Syed
(74) *Attorney, Agent, or Firm* — Nasr Patent Law LLC; Faisal K. Abou-Nasr

(57) ABSTRACT

The disclosure describes an on-demand web-based software and hardware platform that has been developed, on a custom hardware (server) architecture, in an abstracted fashion to enable the administrative users (admins) to create and deploy their experience that can manage asynchronous communication and decision-oriented workflows, in a secure fashion, within a healthcare system. The experience created by the admin can be used for almost any use-case (within care delivery, care coordination and care management) where asynchronous and decision-based workflows and video-centric asynchronous communication proves to derive value resulting in increased productivity, reduction in cost, improved revenue production. Additionally, from an asynchronous communication perspective, the platform empowers the delivery of "capture, store and forward" video-based one-way, two-way and multi-way user interactivity. And, the admin can use the platform's tool sets to create membership models, product types, page designs and media/content libraries that surround the overall experience being delivered for patients and providers.

16 Claims, 15 Drawing Sheets

Related U.S. Application Data

(60) Provisional application No. 61/878,121, filed on Sep. 16, 2013.

(51) Int. Cl.
*G06F 16/27* (2019.01)
*G06Q 10/10* (2012.01)
*G16H 80/00* (2018.01)
*G06Q 50/22* (2018.01)

(52) U.S. Cl.
CPC ........... *G06Q 10/103* (2013.01); *G06Q 50/22* (2013.01); *G16H 80/00* (2018.01)

(56) References Cited

U.S. PATENT DOCUMENTS

| | | | | |
|---|---|---|---|---|
| 7,970,631 | B2 * | 6/2011 | Bruggeman | A61B 5/682 |
| | | | | 705/2 |
| 9,015,037 | B2 * | 4/2015 | Myslinski | G06Q 30/02 |
| | | | | 704/7 |
| 2006/0172708 | A1 | 8/2006 | Vining et al. | |
| 2007/0003211 | A1 | 1/2007 | Gregory | |
| 2007/0033072 | A1 | 2/2007 | Bildirici | |
| 2007/0116036 | A1 * | 5/2007 | Moore | H04L 67/00 |
| | | | | 370/462 |
| 2008/0275311 | A1 * | 11/2008 | Haq | G06Q 10/10 |
| | | | | 600/300 |
| 2009/0012373 | A1 * | 1/2009 | Raij | G16H 80/00 |
| | | | | 600/300 |
| 2009/0182577 | A1 * | 7/2009 | Squilla | G06Q 10/103 |
| | | | | 705/2 |
| 2010/0010830 | A1 * | 1/2010 | Dai | G16H 40/63 |
| | | | | 348/565 |
| 2011/0137727 | A1 * | 6/2011 | Chung | G06Q 30/0274 |
| | | | | 725/38 |
| 2011/0184249 | A1 * | 7/2011 | Davis, Jr. | A61B 5/0013 |
| | | | | 600/300 |
| 2012/0029303 | A1 * | 2/2012 | Shaya | A61B 5/0022 |
| | | | | 348/E7.083 |
| 2013/0046149 | A1 * | 2/2013 | Gettelman | G16H 10/60 |
| | | | | 600/595 |
| 2013/0060576 | A1 * | 3/2013 | Hamm | G16H 40/67 |
| | | | | 705/2 |
| 2013/0212507 | A1 * | 8/2013 | Fedoseyeva | G06F 3/04842 |
| | | | | 715/765 |
| 2013/0212521 | A1 * | 8/2013 | Fedoseyeva | G06Q 10/00 |
| | | | | 715/781 |
| 2014/0081659 | A1 * | 3/2014 | Nawana | A61B 5/4833 |
| | | | | 705/3 |
| 2014/0164994 | A1 * | 6/2014 | Myslinski | G06F 3/04817 |
| | | | | 715/808 |
| 2014/0365234 | A1 * | 12/2014 | Saunders | G06Q 40/08 |
| | | | | 705/2 |
| 2015/0019231 | A1 * | 1/2015 | Sadler | G16H 10/60 |
| | | | | 705/2 |
| 2015/0046183 | A1 * | 2/2015 | Cireddu | G16H 10/60 |
| | | | | 705/3 |

* cited by examiner

WEB AND MOBILE-BASED PLATFORM THAT UNITES WORKFLOW MANAGEMENT AND ASYNCHRONOUS VIDEO COLLABORATION FOR HEALTHCARE

CROSS-REFERENCE TO RELATED APPLICATION(S)

The present application is a continuation of U.S. Nonprovisional application Ser. No. 14/484,912, filed Sep. 12, 2014, which claims the benefit of U.S. Provisional Application No. 61/878,121, filed Sep. 16, 2013.

BACKGROUND

Software as a service (SaaS) services comprise software delivery methods that provide access to the software and the functionality remotely and is centrally hosted. SaaS software and functionality are typically provided through Web-based services (e.g., accessible through a web browser through the Internet).

SUMMARY

Web/mobile and video technologies have been developed to allow for interactive functionality. Workflow management systems are prevalent in the enterprise setting to handle very specific areas, e.g., sales process, billing cycles, task management, medical record input, etc. integrated video-camera devices and streaming video technologies enable the recording and viewing of video derived from server technology. Server virtualization technologies aggregated into "cloud services" enable the delivery of web and mobile software via various subscription models and in an on-demand fashion for the client or enterprise organization. Content management systems empower users to create, edit, design and deploy their content experiences. E-commerce and payment gateway technologies have effectively enabled the processing of credit cards via web and mobile devices. Reporting tools exist to query databases to devise reports and analytics.

The present disclosure combines and goes beyond these overall concepts and technologies. This disclosure's tools set (sometimes referred to as platform) enables the conceptualization, creation, adaptability, management and deployment of an admin-directed video-based, asynchronous, decision-based workflow and collaboration experience that spans across an entire healthcare system to address many different use-cases. The platform enables the admin to conceptualize an experience he or she wishes to deliver utilizing its tool set and then configure it accordingly.

The present disclosure provides, among other things, asynchronous workflow management, e-commerce tool sets, asynchronous video-based collaboration capabilities, and content management. More specifically, the disclosure manages, among other things, video-based, asynchronous collaboration and interactivity within decision-based workflows in a remote healthcare setting, such as, for example, pre-operative education and surgical coordination, post-operative follow-up and rehab, hospital readmission reduction, chronic disease management, home care management and internal staff training and education. In an example aspect of the present disclosure, the admin can create and deploy one or more of these use-cases within their health system. The system can be built and designed to be use-case agnostic, thus enabling its underlying experience to be self-created and adapted by the admin. This is why the present disclosure is called a platform, as it allows the admin to (a) use it to adapt to their organization's workflow and protocols (use-case), and (b) not require development or programming skills to create their desired experience.

The tool set includes many different features and functionalities; however, they revolve around the ability to create decision-oriented interactive and collaborative workflows that engage one or more users (e.g., providers, office staff, caretakers, patients, nurses, etc.) across the health system. This two-way and/or multi-way method of collaboration and interactivity is delivered asynchronously and its process is managed by the platform's queue item management system or "Task System." The present disclosure provides a new paradigm for asynchronous video-based workflow and collaboration across one or many users within the health system.

The present disclosure empowers many capabilities, such as for example: the delivery of pre-determined automated and/or progressive workflows combined with video recording and viewing tools, which are systematically managed by a unique user and group task system, enabling efficiency of the asynchronous flow of data. Or another example, to further the admin-directed experience, the present disclosure integrates complementary web or mobile third-party software technologies. Here are just a few integrated technologies examples: electronic medical record software, practice management systems, billing systems, wireless hardware devices for tracking biometrics, interactive video tools and synchronous video technologies.

The present disclosure can be delivered and reside on a privately owned and fully customized HIPAA-compliant, virtualized server architecture, which is configured to enable a Platform-as-a-Service (PaaS) server environment, also known as the disclosure's "private cloud." The PaaS solution stack enables the development of HIPAA-compliant web and mobile applications, whereas these applications' intention is to integrate into the present disclosure's application programming interface (API).

Additionally, actions enable if/then statements, conditional statements and time-based triggers to an action.

Figure 7:
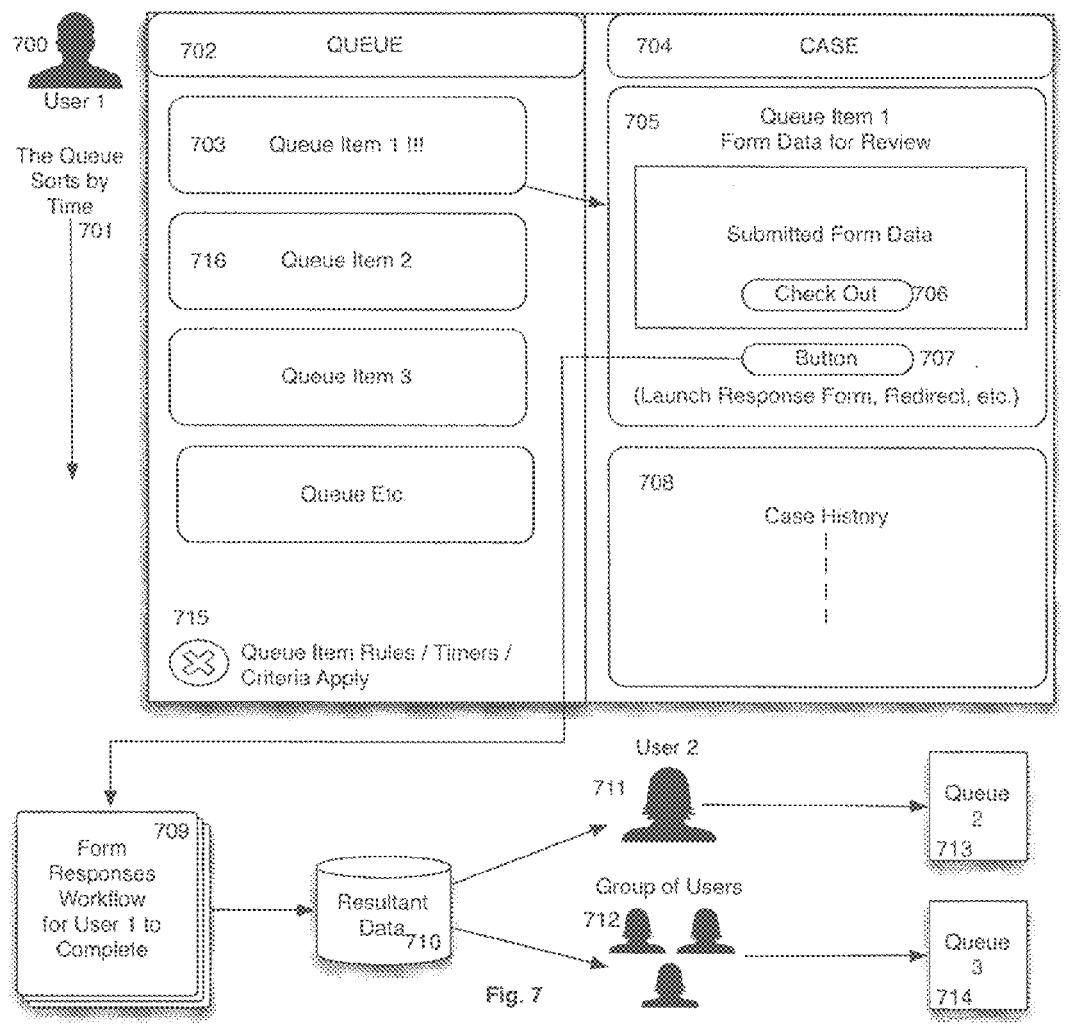

FIG. 7. is a block diagram showing an example embodiment of queues, showing how to manage asynchronous collaboration, as tasks are systematically managed and aggregated for processing by one or more users.

Figure 8:
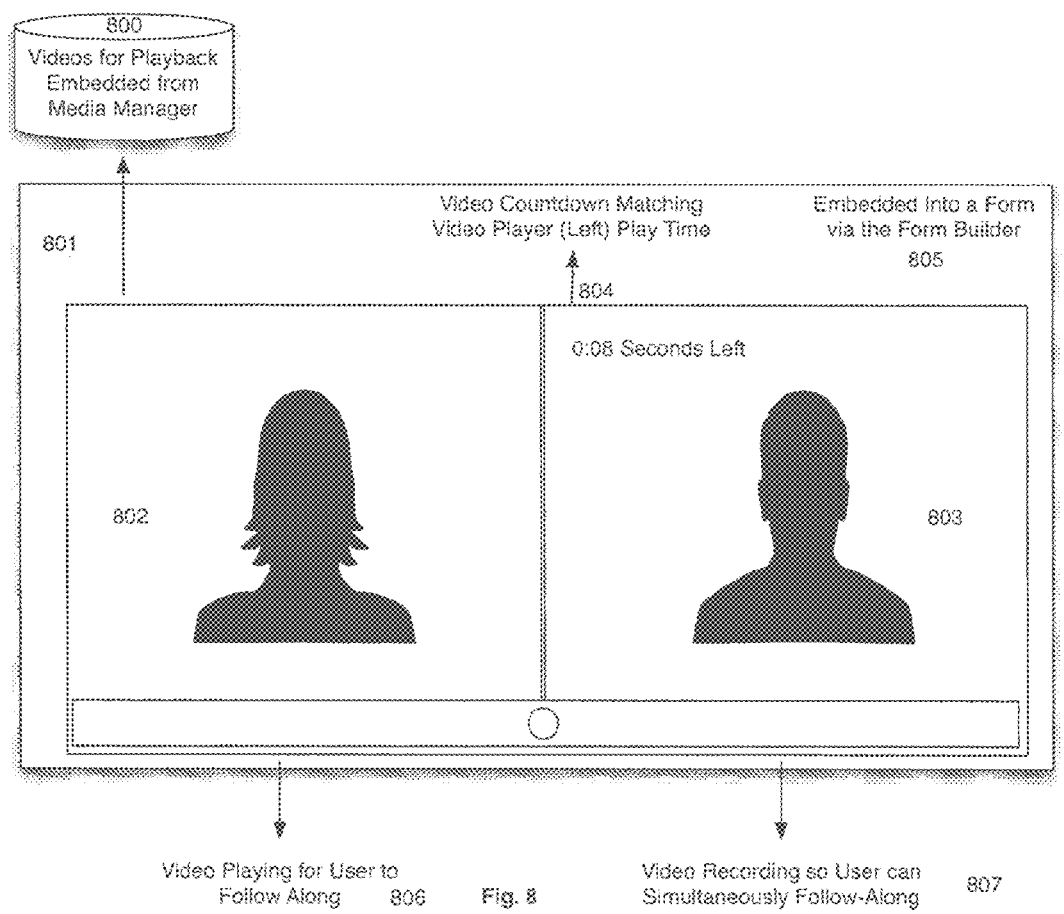

FIG. 8. is a block diagram of an example embodiment of a side-by-side video recorder, which enables users to capture visual data (record), while following along with a model in a playing video, whether its conducted simultaneously or sequentially.

Figure 9:
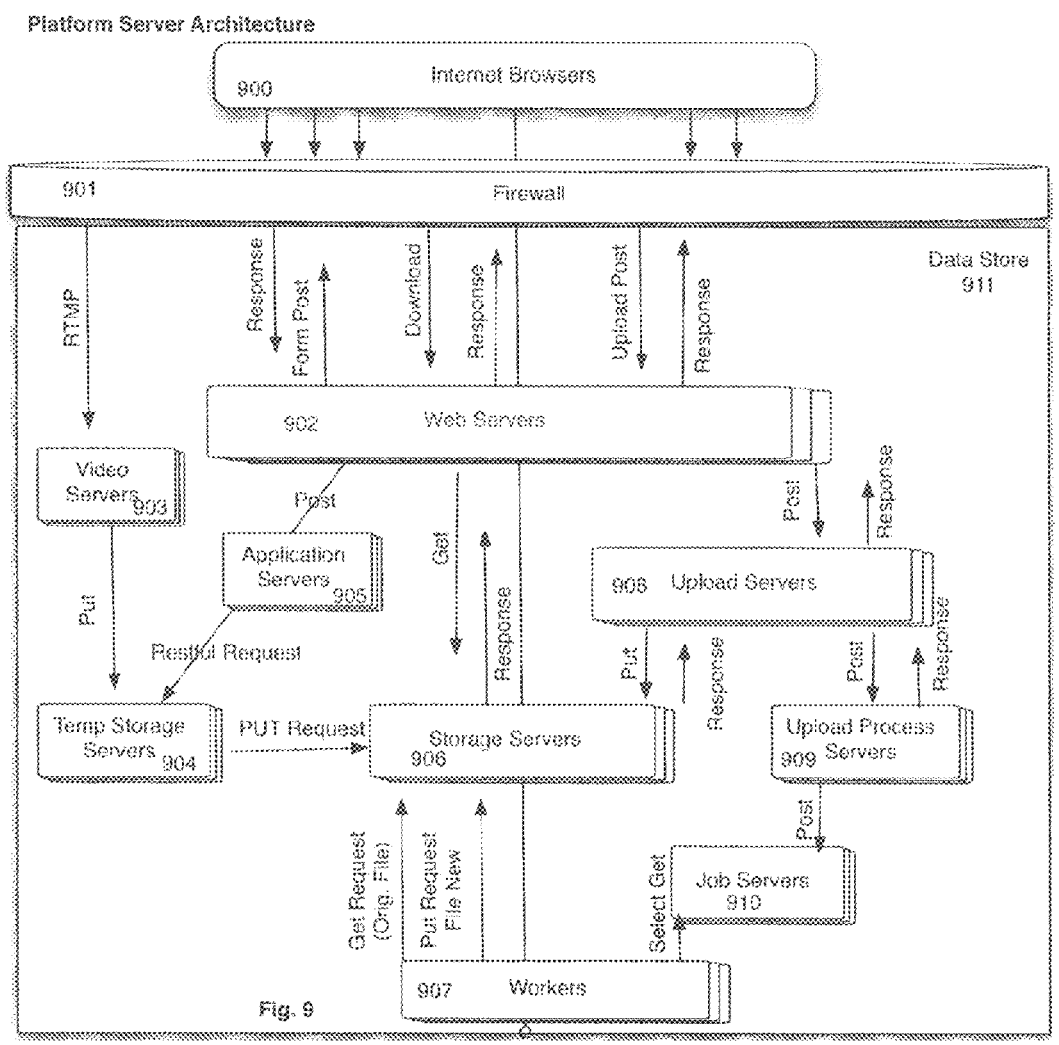

FIG. 9. is a block diagram of an example embodiment of the platform's custom system architecture depicting how all the components and capabilities (above FIG. 1-FIG. 8 and related description) are connected and processed.

Figure 10:
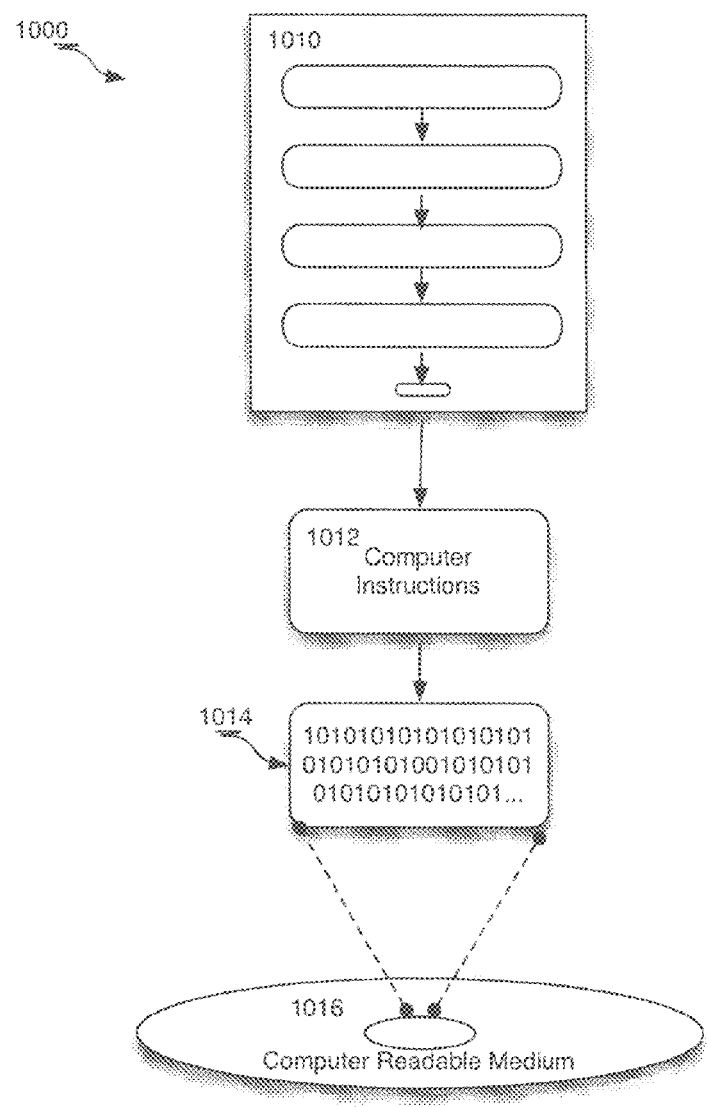

FIG. 10. shows an exemplary computer-readable medium that may be devised to implement embodiments of one or more of the disclosures presented herein.

Figure 11:
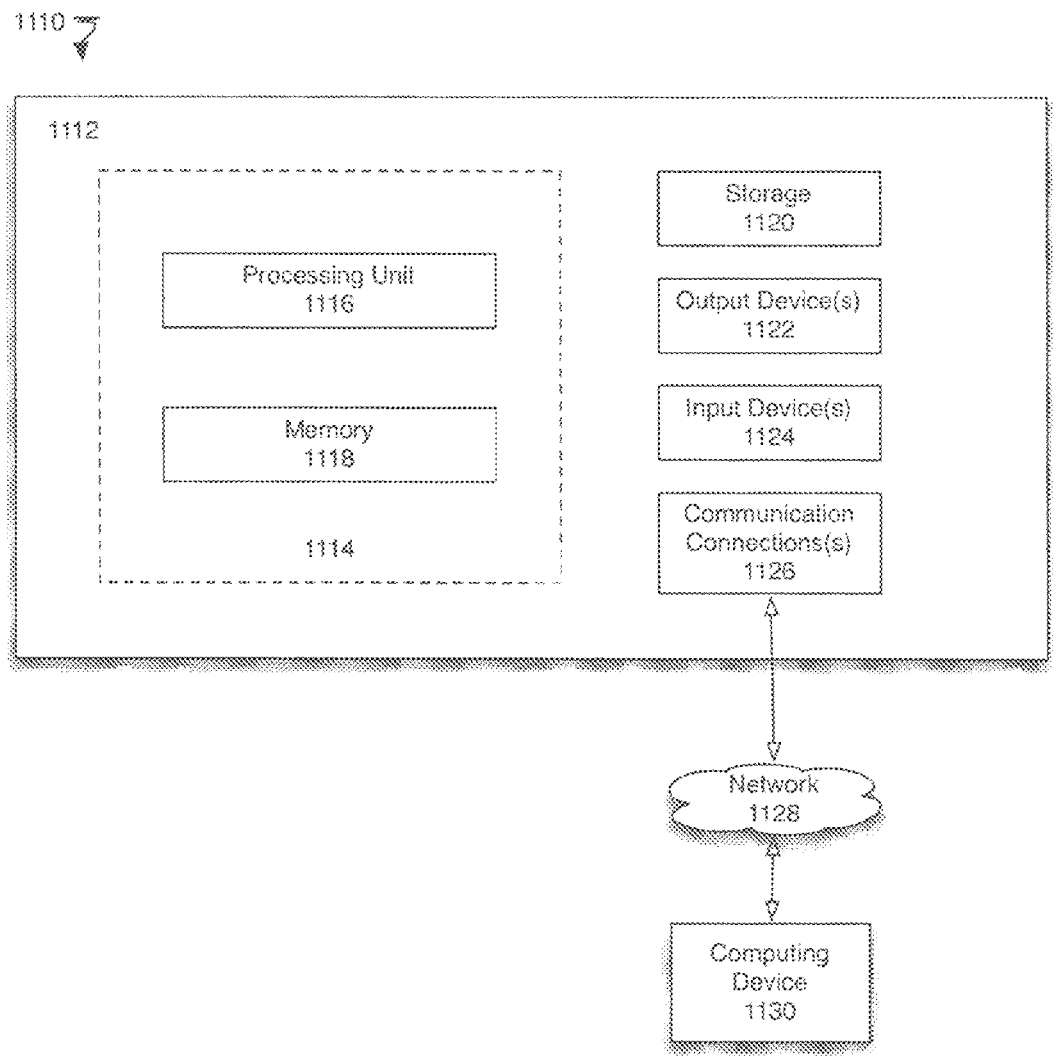

FIG. 11. shows an exemplary system or computing environment to implement embodiments of one or more of the disclosures presented herein.

Figure 12:
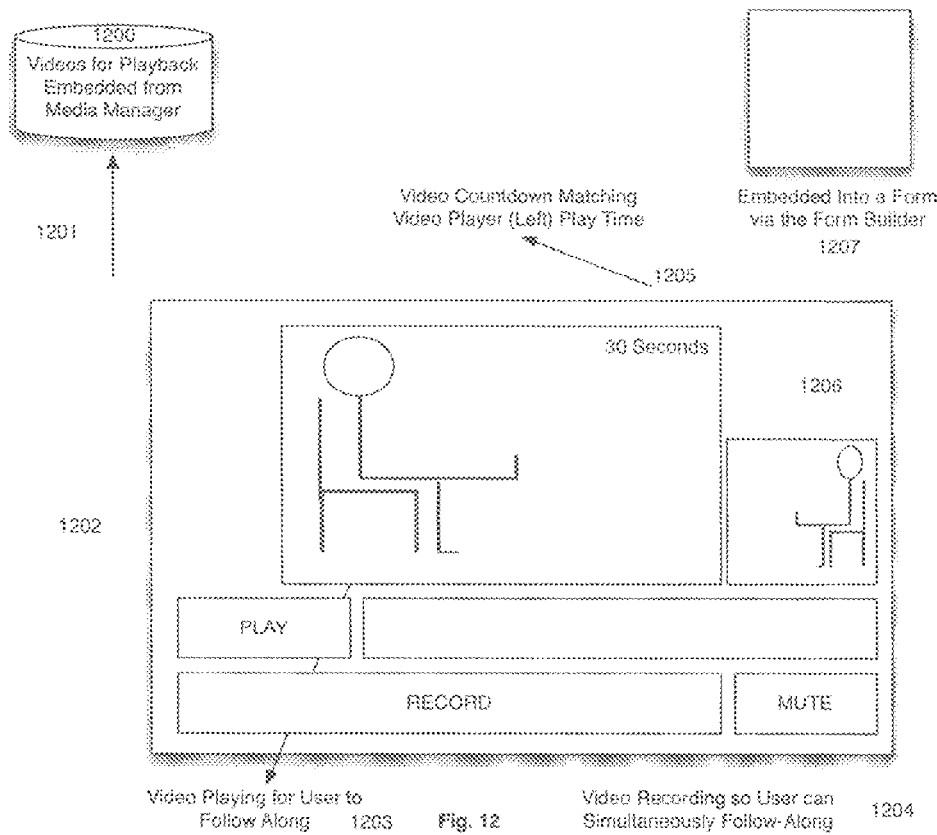

FIG. 12. is a block diagram that depicts the web and mobile picture-in-picture video mirroring recorder, enabling a user to follow along with a pre-recorded video while recording him or herself simultaneously.

Figure 13:
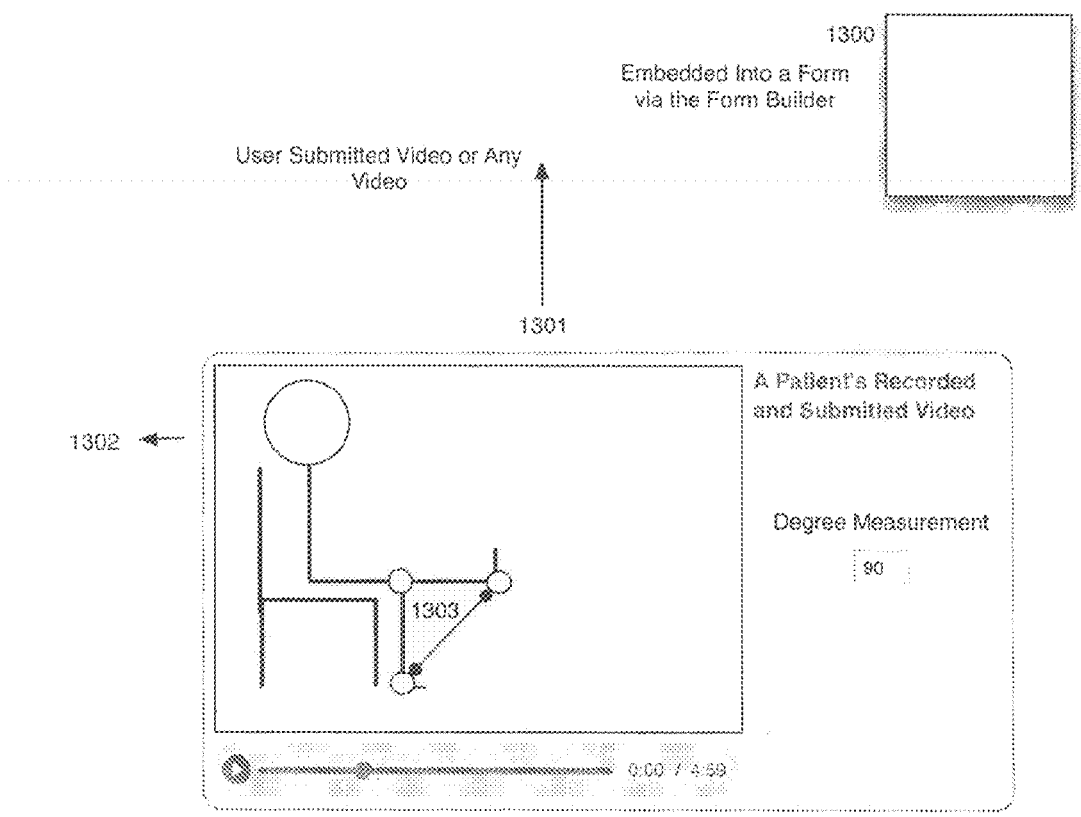

FIG. 13. depicts an HTML-5 video player that enables the user to manipulate the video by drawing an arbitrary angle, while automatically capturing and redirecting the resultant angle data to a field within the platform of another third party API integration.

Figure 14:
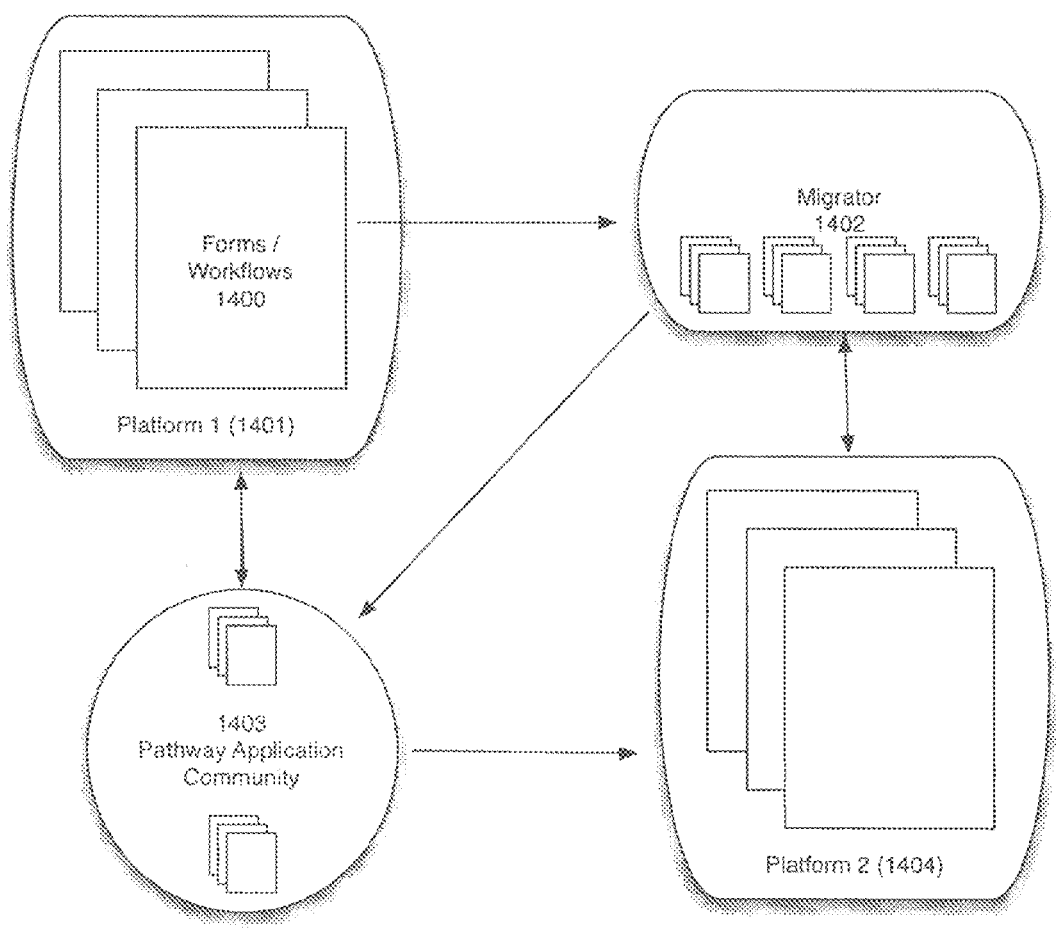

FIG. 14. is a diagram of the migrator, which enables a user (with permission) to copy any set of forms, workflows (pathways) from one platform to another platform. Additionally, the diagram depicts the pathway application community where platform owners can browse, access and optionally purchases a pathway from another platform owner.

Figure 15:
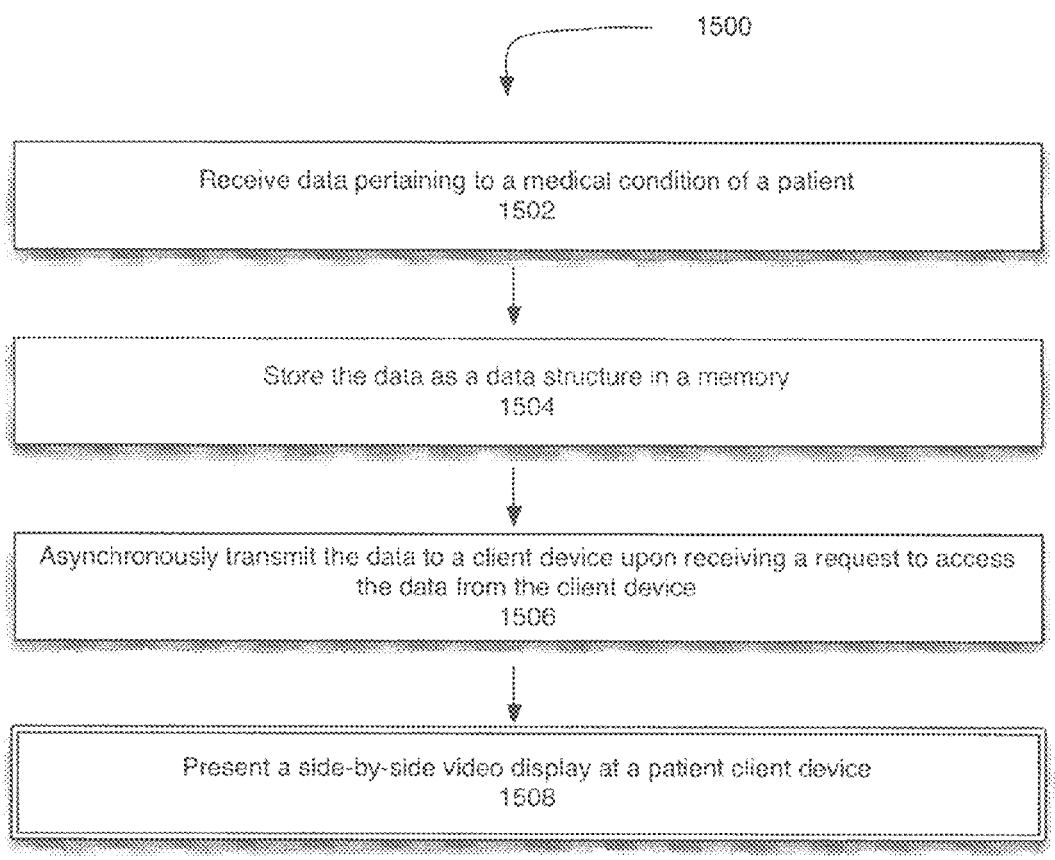

FIG. 15. is a flow diagram illustrating an example method for performing asynchronous communication in accordance with an example implementation of the present disclosure.

DETAILED DESCRIPTION

With the Internet's software movement and advancement toward Platform-as-a-Service (PaaS) and Software-as-a-Service (SaaS), enterprise organizations are utilizing these on-demand software applications to improve and enhance their end-users' experience, productivity, revenue production and cost reduction. Healthcare is no different. With major policy changes in healthcare (i.e., the Affordable Care Act), preventative-care, patient engagement, care coordination and telehealth technologies need to become more accessible, interoperable, consolidated for the Health System or Healthcare Organization. As the Affordable Care Act currently takes effect across the United States, more patients require additional care, and there are not enough healthcare providers to manage the care of the current population, let alone an influx of new patients. To accomplish this feat in the manner that the Affordable Care Act was written (i.e., increase patient engagement, access to care, education and quality of care), it's innovative technology that can and will make this possible across large populations of patients.

The workflow management and asynchronous video collaboration platform described herein is making its impact with these efforts. Providers (doctors, physician assistants, nurses and care coordinators) have fixed time in the day to see a finite number of patients.

The asynchronous video collaboration workflow engine described herein enables two different types of use-cases: substitutional and supplemental. Within a substitutional use-case, the asynchronous video collaboration workflow engine replaces the need for uneventful follow-up visits, and from the patients' perspective, the patients are freed from the hassle and expense of missing work and wasting hours of time for a very brief uneventful in-person visit. A patient is directed when and instructed how to record a video follow-up visit from anywhere and on any device. After the patient completes his/her follow-up task, it is submitted (stored and forwarded) to the appropriate provider, such as for example a specialist, physician assistant, primary care physician (PCP), or physical therapist (PT) for review and response. Since approximately half of providers' workdays are devoted to follow-up visits and the wide majority of those visits are uneventful and non-reimbursable, healthcare organizations and providers have a significant opportunity to improve efficiency, optimize time and drive new revenues. To drive revenue opportunities, providers free up slots in their schedules for new patients, which convert to new surgeries and other billable procedures. With the asynchronous video collaboration workflow engine described herein, unnecessary in-person follow-up visits with the provider go from about 15 minutes or more to remote recorded visits taking less than about 3 minutes to complete and respond to the patient. Since the interaction is conducted in an asynchronous setting, providers review and respond with pre-recorded or real-time recorded video messages. Some other use-case examples include post-operative follow-up and care management follow-up.

Within a supplemental use-case, the workflow engine enables providers, such as for example care coordinators, care managers, and physical therapists to automate the delivery of programs, such as for example interactive care/rehab management protocols. Providers stay informed with the patient's program. At desired intervals throughout the course of the program, the appropriate providers personally communicate with the patient and one another via interactive, store-forward video to provide on-going treatment, encouragement, positive reinforcement and education. Additionally, the platform's content management system enables providers to create a robust, organized and tailored hub of educational/resource content. Provider teams will be able to collaborate to drive better outcomes, improve efficiency of care, and track system-wide success metrics. Through customizable risk assessment forms, providers can automatically enroll patients into automated disease management programs that employ and coordinate appropriate care team members based on desired outcomes for that specific patient. Providers engage more patients within their existing time constraints, and interact with them more frequently, while more effectively managing the highest priority patients. Through the automation capabilities described herein, one provider may yield the productivity of about three or more of their peers that are not using the workflow engine described herein within the same timeframe, thus significantly scaling management of the patient population. Some supplemental use-case examples include chronic disease management, physical therapy, and wellness.

Additionally, with the platform described herein, it goes beyond simply patient/provider interaction, but also extends into internal/external coordination within the health system. It increases efficiencies and accountability across the organization as it relates to providers, patients, administrators, nurses, etc., by streamlining workflows and automating and tracking them for all parties involved. Now, major issues like post-operative follow-up, rehabilitation, surgical coordination, chronic disease management and hospital readmissions can all be addressed under one adaptable platform, utilizing the same user experience no matter what use-case the health system uses the platform.

Reference will now be made in detail to several embodiments of the disclosure that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the disclosure in any manner.

Figure 1:
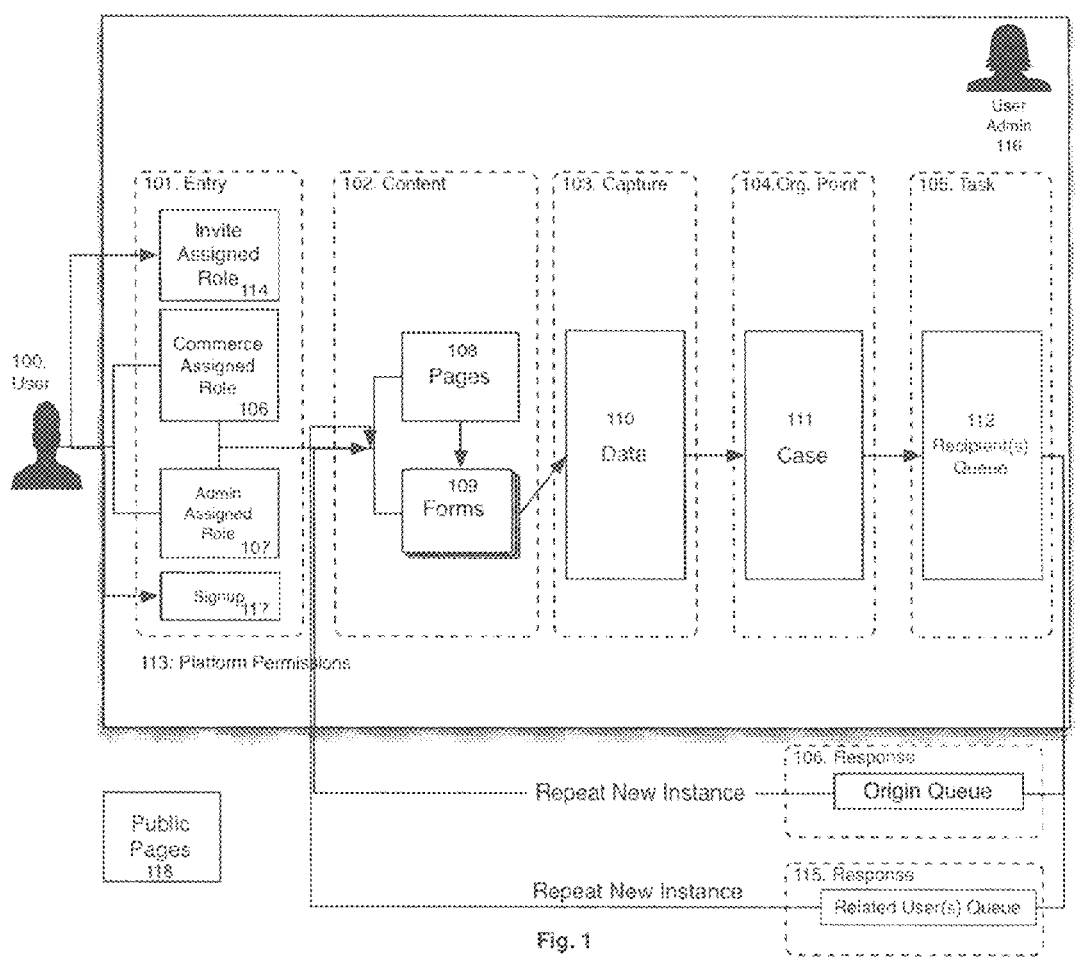
FIG. 1. is a block diagram showing an example embodiment of this disclosure of a platform information flow, showing an example of how data is derived and flows through the platform.

An example embodiment of the platform's information flow is illustrated in FIG. 1. Users [100] can enter the environment [101] through a number of different ways [106, 107, 114, 117]. In the simplest way, the user [100] has an account created for them by a sufficiently privileged admin [116] (e.g., an administrator), which is a role, derived from permissions [113], that is assigned to a user [100]. Admins [116] receive this permission through the platform's permission system [113]. The admin can choose to give the user [100] a role, which classifies the user [100] and assigns an administrator-defined set of permissions [113]. In this way, users [100] can become one or more pre-determined roles, e.g., doctors, nurses, administrators, contributors, etc. User [100] entry can also be self-driven via a signup [117]. Users [100] can either create their own account (if the environment is configured to allow such behavior), or they can purchase membership (a role) to the environment [106] or they can be invited [114] by another user with permission to do so. The commerce system [106] allows for one-time, as well as interval-based billing, meaning that roles can be sold, and various levels of permissions [113] can be sold as well.

Content [102] within the environment can be broken down into two overarching categories—pages [108] and forms [109]. Pages [108] are created and designed with the platform's page builder (discussed in FIG. 3) and represents both static and dynamic information. Forms [109] are built with the platform's form builder (illustrated in and discussed with respect to, for example, FIG. 4) and are used to gather data [110] from the user. Forms [109] can optionally have their captured data [110] designed with the form data designer (illustrated in and discussed with respect to, for example, FIG. 3), enabling the system to act as a self-generating content management system (illustrated in and discussed with respect to, for example, FIG. 3). A sufficiently privileged user, such as an admin [116], can create a form [109] or a series of forms [109] to represent a page or pages [108] of information, and then can use the form data designer (illustrated in and discussed with respect to, for example, FIG. 3) to design the output of that form [109]. In an implementation of the present disclosure, a difference between a page [108] and a form [109] is that forms [109] gather information from users [100], whereas pages [108] are passive, existing to present information, never gathering it, as well as can be for public use outside the platform [118].

Forms [109] are filled out, using fields (illustrated in and discussed with respect to, for example, FIG. 5) that were placed into a form during the form builder process (illustrated in and discussed with respect to, for example, FIG. 4), and submitted by users [100]. The resultant data [110] is captured, logged, stored and routed by the platform's underlying server architecture (illustrated in and discussed with respect to, for example, FIG. 9). Depending on the context or use-case (illustrated in and discussed with respect to, for example, FIG. 2), data [110] can be used in various ways throughout the system to enable collaboration and communication between multiple users [100]. Data [110] is most useful when it is organized in a human-readable format (top to bottom and utilizing, but not limited to, text, pictures, videos and file attachments). Videos are enabled by the platform's ability to capture data [110] in visual format using various video recording fields (illustrated in and discussed with respect to, for example, FIG. 5 and FIG. 8).

The organization point [104] is utilized to structure data within the platform. Cases [111] are utilized to organize captured data [110] relating to a user [100]. The cases [111] have an owner—the user [100] that the case [111] is ultimately related to. Data [110] can be sent via actions (illustrated in and discussed with respect to, for example, FIG. 6) to a user's [100] case [111], though the data [110] does not have to originate from the user that owns the case [111]. In this way, a healthcare provider can update a patient's case [111] without being the owner of it. Cases [111] are therefore used to group data [110] from various different sources in a way that makes sense given the context or use-case (e.g., a post-operative follow-up program, illustrated in and discussed with respect to, for example, FIG. 2). Within the platform's server architecture (illustrated in and discussed with respect to, for example, FIG. 9), case data [111] can be encrypted and segregated across servers or devices to ensure privacy and security.

The task [105] enables the asynchronous collaboration to exist. Respective users [100] and groups (illustrated in and discussed with respect to, for example, FIG. 2) within the platform has his or her own queue [112]. Queues [112] are repositories for queue items (e.g., tasks) (illustrated in and discussed with respect to, for example, FIG. 7). As the user [100] completes these queue items (illustrated in and discussed with respect to, for example, FIG. 7), they are routed via actions (illustrated in and discussed with respect to, for example, FIG. 6) to other users' queues [115] or launch a form [109] to the origin queue [106] or to the same user's [100] queue creating a workflow (illustrated in and discussed with respect to, for example, FIG. 2).

The response [106] represents the manner in which the flow of data [110] from one user's queue [112] to another can be self-perpetuating and circular. For instance, in order to complete a queue item (illustrated in and discussed with respect to, for example, FIG. 7), a user may fill out a form [109]. The form [109], in this example, has actions (illustrated in and discussed with respect to, for example, FIG. 6) associated with it that initiates a new queue item (illustrated in and discussed with respect to, for example, FIG. 7) to the related users' queue [115] or to that user [100] that just completed the queue item (illustrated in and discussed with respect to, for example, FIG. 7). This flow of information is configurable, and can establish the various experiences that can be implemented within the platform or use-cases (illustrated in and discussed with respect to, for example, FIG. 2). We call this data flow a workflow (illustrated in and discussed with respect to, for example, FIG. 2). Workflows enable, for example, program automation and/or progressive automation, thus providing the ability to create care and training programs that run its directed course; engaging the appropriate users' queues [112, 106, 115] along the way for feedback and interaction; and the appropriate reporting and tracking (illustrated in and discussed with respect to, for example, FIG. 2) information regarding the users involved within the workflow.

Figure 2:
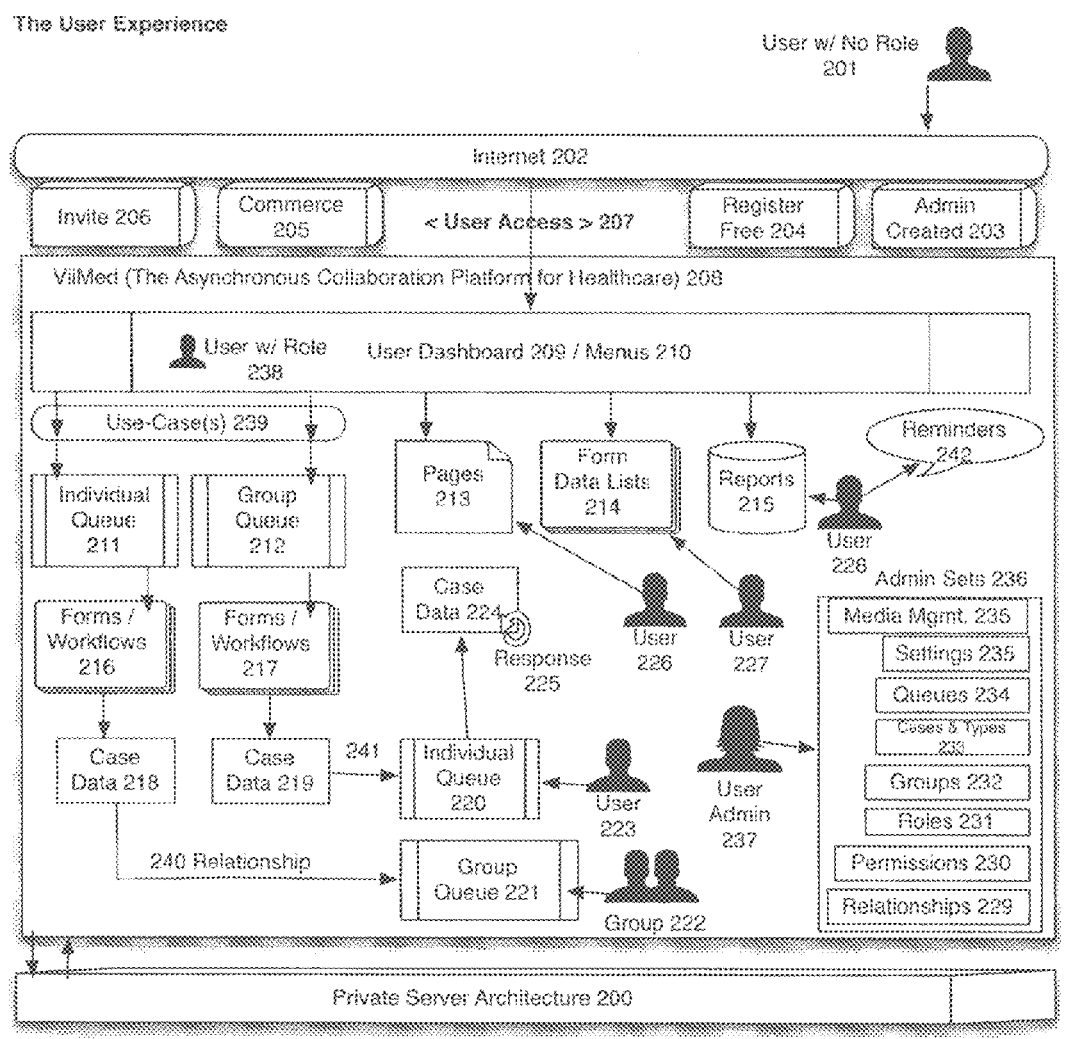
FIG. 2. is a block diagram showing an example embodiment of this disclosure of a user experience inside the platform, showing an example of how the user manipulates and can flow through the platform.
Figure 3:
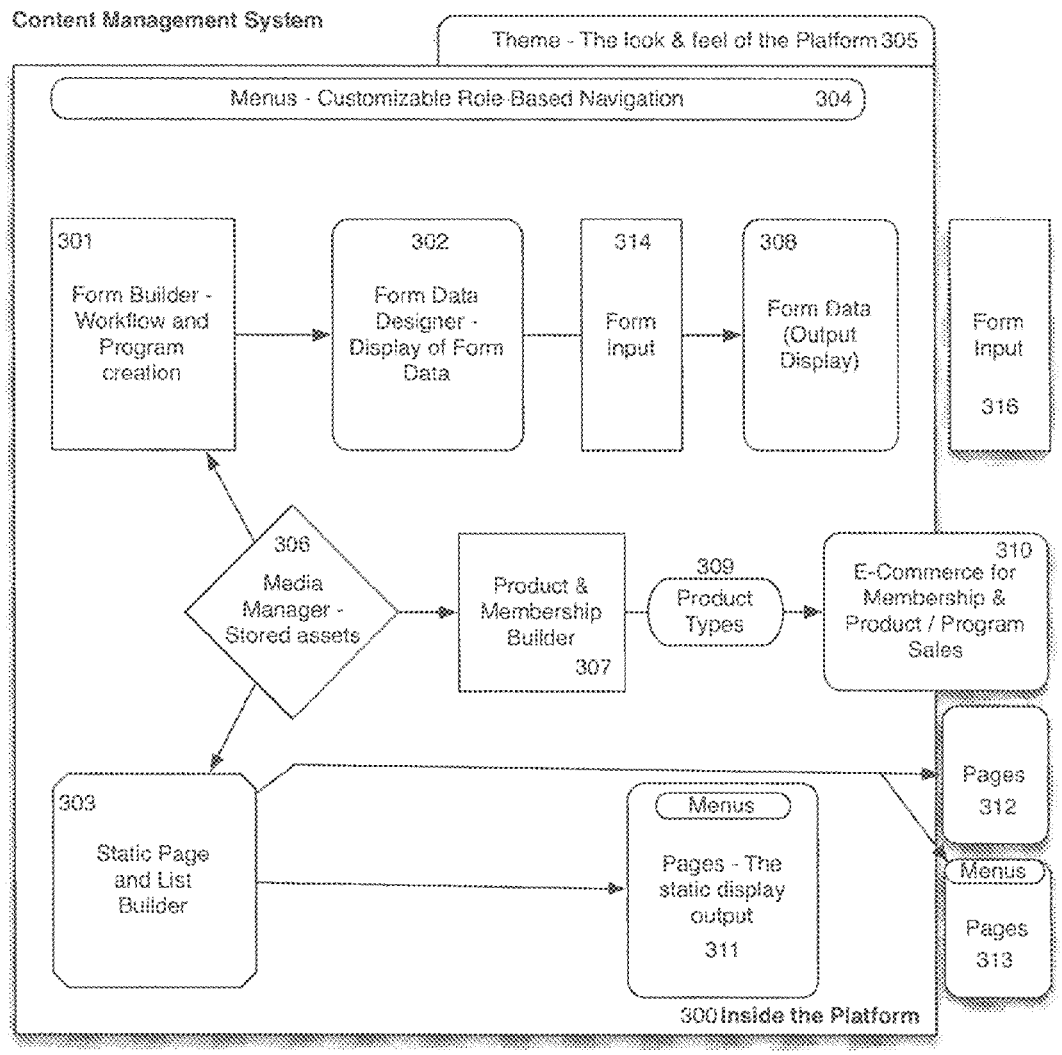
FIG. 3. is a block diagram showing an example embodiment of this disclosure of a content management system, showing an example of the platform's content and media posting capabilities.

The user experience [FIG. 2] inside the platform depicts how users maneuver through the platform. User [201] is a user without a role. Roles are defined by admins [237]. Once a user without a role [201] decides to become a user with a role [238], he or she can enable this to happen in one of four ways. Admin created [203] enables admins to create the user's account and assign a role [231], which will give the user access [207] and drop them at his or her dashboard [209] where there will be a menu [210] of items to choose from. Now user with a role [238] is considered a member. A role [231] can be purchased via the commerce system [205], or invited by another user that already has a role [226, 227, 228, 223, 237]; however, the user must have permissions [230] assigned to them by the admin [237] to send an invitation to a user without a role [201]. Roles [231] are used to group alike users together. Roles [231] can have any name, and can grant any arbitrarily designated set of permissions, which are defined by the admin [237]. Permissions [230] are the privileges granted to a user [200]. Permissions [230] are both role-based and contextual. That is, permission-sets can be granted to users with a specified role [231]; however, certain permissions [230](such as, for example, access to a given piece of patient data [218]) can be granted in a context-specific situation. For instance, a doctor may not be able to view all data within the system, but may be granted permission [230] to view an individual patient's data [218] via a relationship [240, 241], which was derived from the settings found within [229]. Role-based [231] permissions [229] enable server architecture (illustrated in and discussed with respect to, for example, FIG. 9) to process compliance needs appropriately, e.g., Health Information Portability and Accountability Act (HIPAA) Compliance.

Since the user [238] has been provided a role, the user [238] can navigate the system through, in some implementations a pre-determined, use-case [239] that may have different interactions associated with it. Other users [222, 223, 226, 227, 228, 237, etc.] can be related, via use-case [229], to the user [238], pages [213] can be accessible to the user [238], form data displayed in lists [214] can be viewed by the user [238] (which can display libraries of media), certain reports [215] can be viewed by the user [238] if he or she has permission [230] via role [231] to do so, and the user [238] can view his or her reminders [242] that have been derived from actions (illustrated in and discussed with respect to, for example, FIG. 6). The user [238] can begin his or her use-case [239] and is presented with his or her individual queue [211] or group queue [212], where he or she will find queue items (illustrated in and discussed with respect to, for example, FIG. 7) to complete. The user [238] views a queue item, which takes him or her to a form or set of forms [216, 217]. The user [238] completes his or her queue item, which either forms a new case [218, 219] or adds to a current case [218, 219] owned by another user [226, 227, etc.] within the platform [208]. Completing the queue item from [211 or 212], not only creates or adds to a case [218, 219], it also can initiate actions (illustrated in and discussed with respect to, for example, FIG. 6), that send a subsequent queue item to other users' queues [220, 221] for that user [223] or users [222] to access, triage and complete, therefore continuing the use-case [239] and creating their case data [224]. Now, because admins [237] can use the various aspects of the platform's [208] media management [235] (illustrated in and discussed with respect to, for example, FIG. 4) to conceptualize and derive their use-case [239], which can be decision-oriented and engage different users along the way based on user's [238] decisions within the forms/workflows [216, 217]. This navigation through a user-ca-e [239] can be implemented, for example, through the platform's [208] underlying server architecture, which is illustrated in and discussed with respect to, for example, FIG. 9.

Discussing the queue [211], forms/workflows [216], and cases [219] in more detail, as discussed, forms [216] are used to capture data [218, 219] from users [238]. The tree-like structure of the forms (illustrated in and discussed with respect to, for example, FIG. 4) allows the use-case's [239] admin [237] to make decisions regarding a course of action for the user [238]. Data [218, 219] exists in many forms—from simple numeric or textual information, to complex data such as recorded video, uploaded files, or touch-based signatures. Data [218, 219] is encrypted during transmission and at-rest using encryption, for example, aes256-bit encryption, all enabled by the private server architecture [200]. Cases [218, 219] may comprise of related queue items (illustrated in and discussed with respect to, for example, FIG. 7) and found in related queues [220, 221], their resultant data (captured when forms are submitted), and activity logs. Cases [218, 219] are owned by an individual user, and are unique per user and case type. Case types [233] are created by administrators [237], and allows the platform to track and group any type of data [218, 219] within cases, from technical support to disease-specific information. Within the depicted diagram, the resultant data from [218, 219] is associated with a given case. Relationship [240, 241] is the relationship of the workflow, which determines the recipient queue [220, 221]. The recipient queue [220] is an individual user's queue. The associated case [219] may or may not belong to the owner of the queue [223], depending on the configuration of the workflow by the admin [237]. For instance, the individual may be a patient's specialist. The case would be associated with the patient, though the queue item (aka task) may be assigned to the patient specialist. The individual that owns the queue will be granted access to either part of the case, or all data associated with the case, depending upon the specific implementation of the workflow. The individual queue [220] organizes queue items assigned specifically to that user [223], until they are completed. Case data [218] can be assigned to a group queue [221], which means that a group of users [222] will have access to the queue items associated with that queue [221]. In an implementation, a difference between an individual queue [220] and a group queue [221] is that the queue item is no longer assigned to a single user. Instead the queue item exists once for the entire group [222]. Any member of the group [222] can perform the associated queue item within the group queue [221]. This allows for flexibility in the way that workflows are designed and configured, as sometimes it makes sense for a queue item to be completed by the first user within a group able to perform the queue item, while other times tasks are best assigned to specific individual users. Additionally, queue items can have binding actions (illustrated in and discussed with respect to, for example, FIG. 6), which may require a set of user(s)/group(s) to complete a queue item that aggregate into a one master queue item that results in being completed. This may prove useful in settings where multiple parties may need to complete their task before the job is actually done, e.g., a surgical center's central booking office may need to ensure a patient visit (queue item 1), the rehab center is scheduled (queue item 2), and prescriptions have been ordered (queue item 3).

Now that the explanation behind the workflow of the platform [208] has been explained, we can further explain how content and workflows are generated by the admin [237]. Let's start with the content management system [FIG.

3]. The form builder [301] is the key component used to build the specific use-case [239]. The form builder [301] allows sufficiently privileged administrators to create forms for both content list [214] building and directed workflow creation. In form input [314], a form is created to capture data that is displayed as content to a user within a use-case [239]. The administrator [237] that creates the form is free to include any type of field to hold various types of data (see more on fields illustrated in and discussed with respect to, for example, FIG. 5), such as text for the page title, body content, a featured video, categories, tags, etc. Form data designer [302] is used to design the visual output of the form data. The form data designer [302] allows the designing admin [237] to choose the look and feel of the data [308] collected by the form [314]. This allows the admin [237] to create one design that can be populated with a variety of information, such as the layout of a video resource page. The page builder [303] is used to create a static page [311, 312, 313]. A static page [311, 312, 313] is not populated with content from form data, instead it is a stand-alone page created and edited directly on-screen. This is best used for informational or marketing-based pages, and allows for the rapid creation of content with minimal technical expertise. Menus [304] can consist of primary, secondary, and tertiary navigation menus and are configured by admin's [237] with sufficient privileges. The platform allows for admins [237] to create nested, hierarchical menus, and offers spaces within the site-wide theme [305] that conform to best practices for interface usability. Likewise, menus can also be embedded directly into data-driven and static pages [311, 313] via the page builder [303]. Aspects of the navigation can be specified on a per-role basis, allowing different experiences for users with different roles. Theme [305] is the overall theme of the environment and can be set by the admin [237] within the platform's [208] settings [235]. The look and feel of the overall environment can be customized to match the branding of a specific organization that platform is provided to, which can be called private labeling. Themes [305] are designed to be responsive to the user's viewport (responsive design). This means that the content displayed by the platform can resize and arrange itself properly to fit the screen that is being used to view the environment, be it a traditional PC, tablet, or smartphone. Combining a responsive theme design with the power of the page builder [303] and form data designer [302] allows people with no knowledge of the responsive design to construct layouts and create content that looks clean and professional across the multitude of devices that are used to access the Internet. Media manager [306] is a centralized repository for frequently used media assets. Media can be pulled into various pages and forms using field types (on forms) and display widgets (on pages) [306 to 301, 306 to 303]. Centralizing certain media assets enables the environment's administrators to save on the transfer of large videos, and enables user's browsers to cache files, making for an overall more efficient experience. Products [307], which can include membership products, can be built through utilizing special field types within the form builder [301]. This enables the customized creation of various forms of membership. Product forms can be designed using the same process as other data-driven pages, allowing a uniform, visually engaging design of products, without the administrator [237] having to learn a new interface. Products can be purchased through the commerce system [310], which supports both one-time and interval-based secure payments. Pages [313, 312], forms [316] and products [310] can be displayed publically, outside the platform [315], as well as inside the platform (where access is derived based on role) [300].

Figure 4:
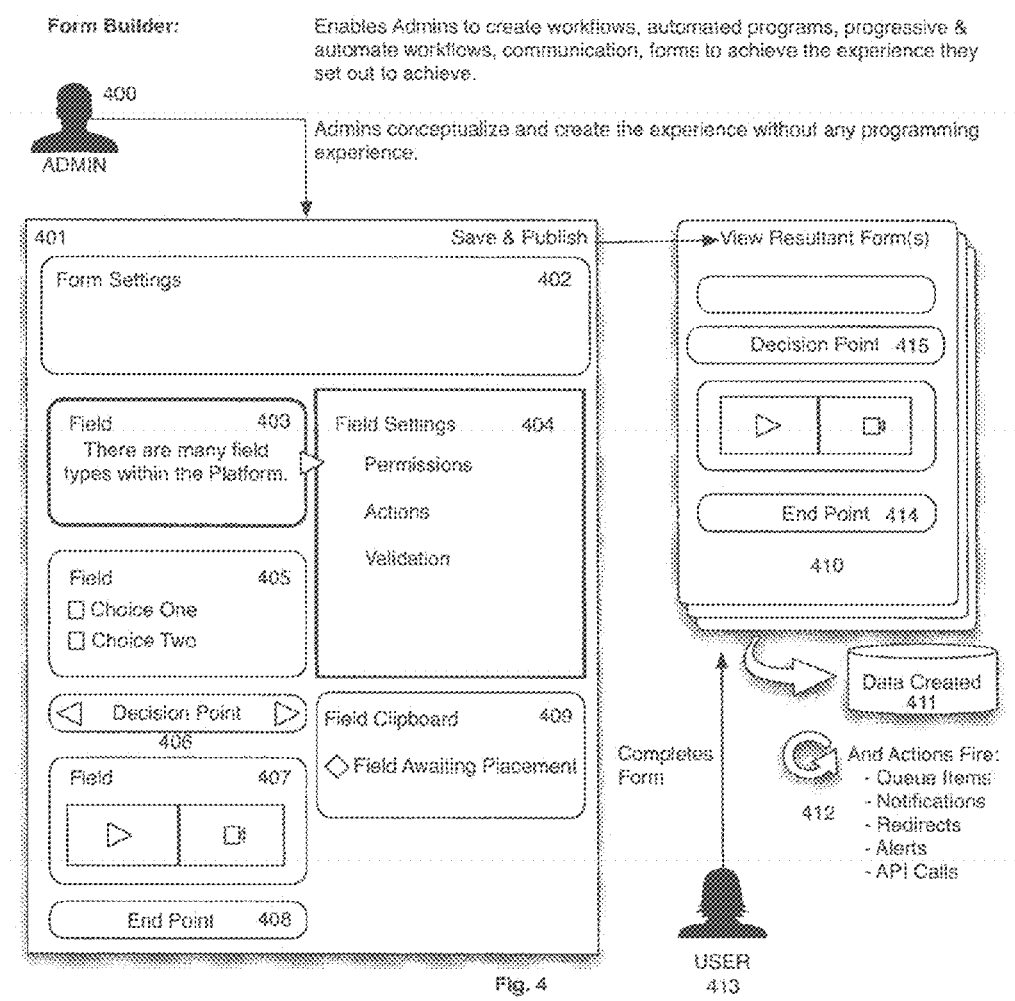
FIG. 4. is a block diagram showing an example embodiment of this disclosure of the form builder, showing an example of enabling the admin to conceptualize, build and make accessible forms combined by actions that create workflows for users within the platform to complete. The form builder enables the platform's asynchronous collaboration capabilities when combined with all aspects depicted in the figures.

In FIG. 4, the form builder displays the end-result of a form [410] created with the form builder. The tree-like nature of the form is not evident to the user [413] filling out the form [410]. While the underlying structure of the form [410] can support many different end points [414] (the final button on a form that performs the actual submission of data), the display merely shows the path through the form that the user is following. The path is determined based on the user's responses to decision points [415], which was derived by the admin [400] during the building process in [406]. The form builder [401] is an interface used to create the forms [410] that make up the vast majority of the use-case [239] of the platform. Forms are created by adding fields [403, 405, 406, 407, 408], and additional fields illustrated in and discussed with respect to, for example, FIG. 5, and by specifying various configuration information [404]. The clipboard [409] is simply used to remove a field from the form, and to place it in a holding area while the form is navigated within the form builder. Fields can be dragged and dropped into the appropriate place within the form builder [401] from the clipboard, enabling fields to be organized and moved around at will. Forms can have many paths through them that a user [400] can choose to take. This is accomplished with decision points [406]. Decision points [406] allow the admin creating the form [400] to essentially create forks in the road of the form. The admin [400] adds a decision point [406] field, and specifies which field [407, 408] comes next based on the answer to the decision point [406] field. In the simplest example, the admin [400] creates a form [410] with a yes/no question. If the user [413] answers yes, the next field that the user [413] sees is different than if the user [413] had chosen no. There is no limit to the number of decision points [406] that can be contained within an individual form, allowing for incredibly complex tree-shaped forms. The end result is that the admin [400] creating the form knows certain information about the user [413] based on the final end point field [414] that the user arrives at. This allows the admin [400] to perform different actions [412] based on this information.

Figure 5:
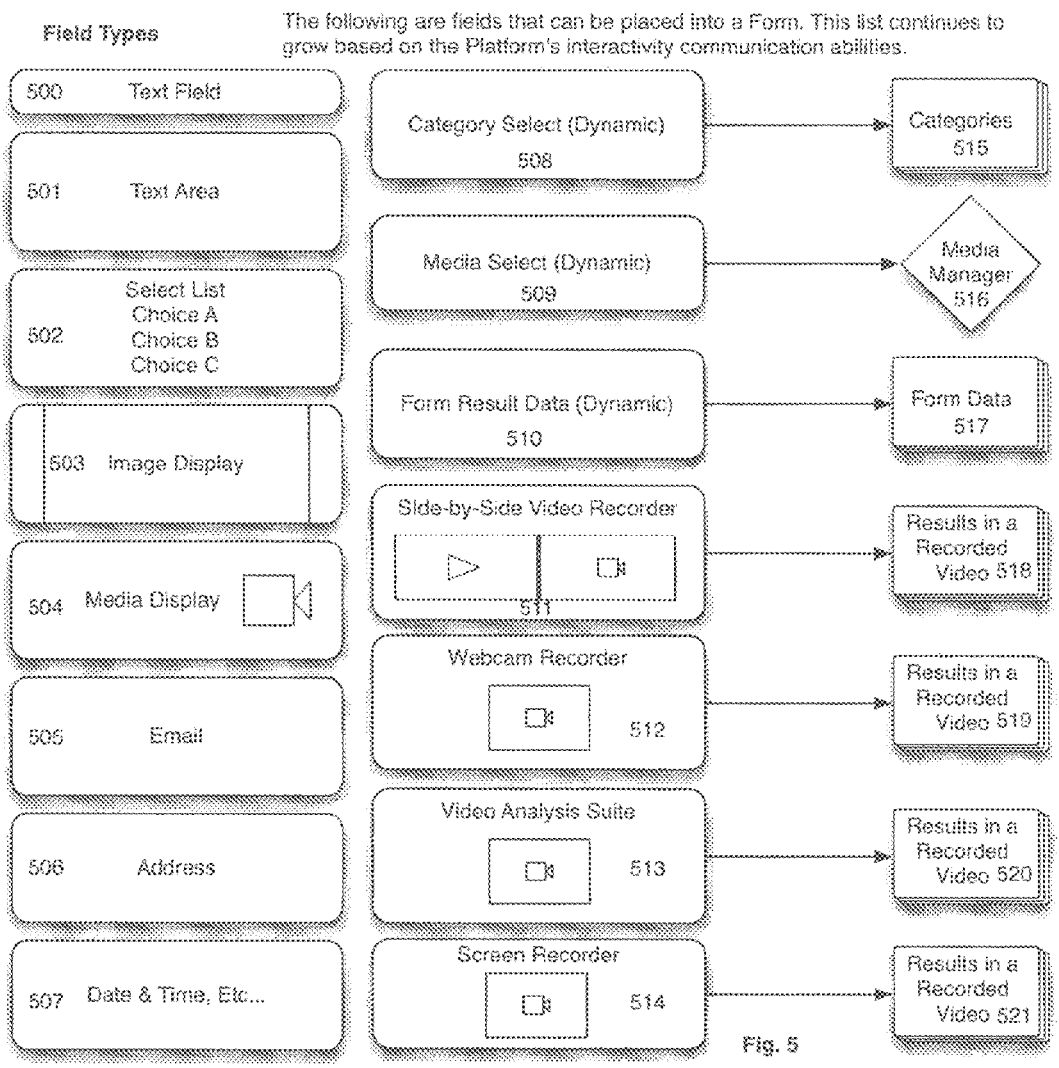
FIG. 5. is a block diagram showing an example embodiment of this disclosure of fields, showing how to enable a form to be interactive.

FIG. 5 relates back to FIG. 4, as field types (FIG. 5) are the individual components that, when combined, make up a form [410]. This is in no way a comprehensive list, as new field types can be continually added to the platform. Field types [FIG. 5] can range in complexity, from simple standard HTML-based text Fields [500], to complex, proprietary side-by-side video recorder fields [511]. All fields are configured and placed within forms using the form builder (FIG. 4). Depending on the field type [FIG. 5], various settings can be configured to control the display and behavior of the field when it is presented to the user. Examples of field type settings on FIG. 4, specifically, field settings [404] range from help text displayed to the user, to the length of time a video recording should last. Fields can optionally have permissions [404] associated with their display, as well as the display of the data collected within a field. This type of granular control over forms allows a single form to contain fields that may be hidden to users with a certain role, yet visible to other users. Validation [404] rules can be setup for individual fields. The most basic validation [404] would be to require a field before the user can successfully submit the form. Other types of validation [404] include the type of information stored within a field (e.g., numeric, alphanumeric, etc.), date-range limits, file types, etc. Validation settings are tied to field types, as certain validations only make sense in certain context (for instance, maximum file size would only make sense when applied to a file upload field type). Actions (illustrated in and discussed with respect to, for example, FIG. 6 or 402) can be tied to fields. Actions (illustrated in and discussed with respect to, for example, FIG. 6 or 402) are processed upon the successful completion of a form [410], after all validation [404] has passed and the end point of the form has been reached [414]. An action [412] is only active in the field that it is attached to be present in the processed form. Since forms can have a tree-like structure, it is entirely possible (and beneficial) for certain actions [412] to be skipped entirely. This allows for drastically different workflows to occur based on the user's data for various fields. Decision points [406] are attached to choice-based field types [502]. The next field to be displayed within the form is based on the answer chosen by the user to the decision point [406]. This enables the tree-like structure of forms [410] to be created within the form builder [401], which in turn enables powerful workflow processes to be created within the platform. For each potential answer to a decision point [406] enabled field, a different route through the form can be defined. There is no limit to the number of decision points [406] within a form, allowing for complex tree-like structures to be created by administrators. Other fields include the webcam recorder [512], which is a video capture field enabling the user to use his or her device's camera as a video recording device, e.g., smartphone, tablets, and/or laptop or desktop webcams. The webcam recorder field [512] is utilized to record and send video messages within the platform. The side-by-side video recorder field (simultaneous) [511] or illustrated in and discussed with respect to, for example, FIG. 8, which is a video capture field enables the user to record him or herself, while simultaneously following along with a video player. What is created is a mirroring effect that provides a simultaneous interactive recording experience. Use-case(s) [239] where a user follows along with an activity (e.g., rehabilitation, post-operative follow-up with a Specialist, chronic disease check-ups with a Primary Care Physician, etc.) provides the underlying value behind the side-by-side video recorder [511] (illustrated in and discussed with respect to, for example, FIG. 8). The side-by-side video recorder (sequential) of FIG. 8 is a video capture field that is the same user interface as the above; however, the side-by-side video recorder can be set to a sequential recording experience for testing environments. The sequential setting directs the user to watch a video from beginning to end without the ability to manipulate the play controls, and upon the video finishing its play routine, the recorder's configured countdown will begin (e.g., 3, 2, 1) and the webcam recorder will capture the user's response. Another interface that represents the same concept as the side-by-side video recorder [511] is the picture-in-picture video recorder (P&PVR) (illustrated in and discussed with respect to, for example, FIG. 12). The differences between the P&PVR and the side-by-side video recorder include the following: the interface [1202] is responsive so it can be used on a mobile device in vertical and horizontal positioning; the user that is recording [1204] him or herself [1206] can overlay the pre-recorded video [1203] if screen space is limited. Conceptually, the use is the same, following along with a video [1203] while the user records him or herself, more specifically, the countdown [1205] measuring how much video will be recorded by the user and the ability to embed videos from the platform's media manager [1200, 1201].

The captured user [1301] video content from these various video recorders are displayed within a form [1300] for a directed or permissible user within a video player [1302], for example an HTML-5 video player [FIG. 13]. Additionally, on the video player, e.g., HTML-5 video player, the viewer of the video can annotate the video with various tools [1303], e.g., angles, area, lines, shapes, and marks.

This specific video capture, utilizing device webcams (e.g., laptops, smartphones or tablets) experience is driven by the platform's server architecture's (illustrated in and discussed with respect to, for example, FIG. 9, 900 to 901, 903, 904, 906) ability to stream video playback, while recording video streams in an encryption methodology, such as for example aes256 bit encryption methodology, in order to meet medical compliance security, e.g., HIPAA Compliance.

Figure 6:
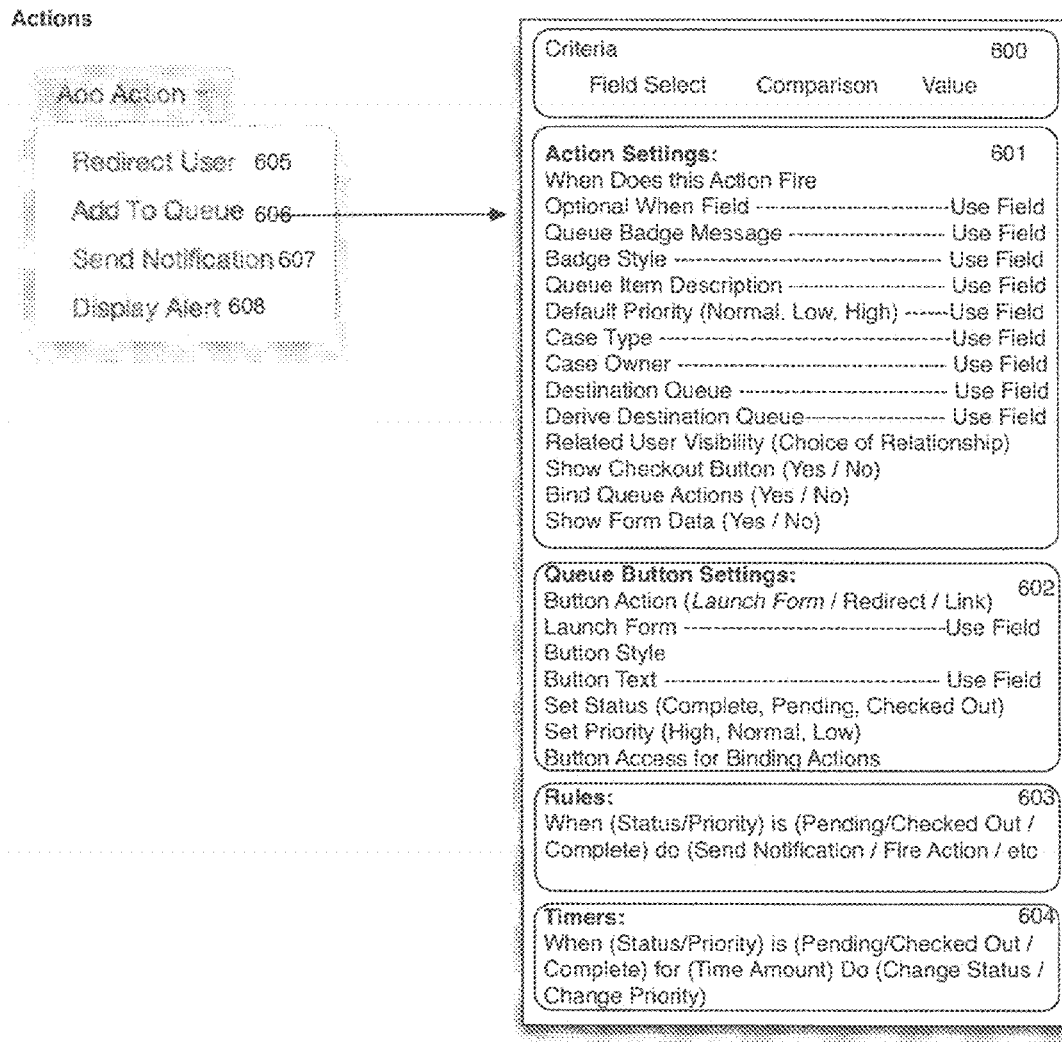
FIG. 6. is a block diagram showing an example embodiment of this disclosure of actions, showing how to provide the form-based triggers that can fire upon submitting a form.

FIG. 4, FIG. 5 and actions [FIG. 6] all relate to one another. Actions [FIG. 6] provide the form-based triggers that can fire upon submitting a form [410]. Additionally, actions [FIG. 6] enable if/then statements, conditional statements and time-based triggers [600, 601, 602, 603, 604] utilizing the action called, add to queue [606]. There are a number of action types within the platform, from notifications [607], redirects [605], alerts [608] and as mentioned the add to queue [606]. Actions can be used to link one form within a workflow to another, redirect the user to a given destination, or send data to an external system via a third-party API. Many actions can be associated with an individual form [410, 412] or field within the form [404], and actions are executed only if the given field exists within the user's instance of the form. This allows the admin [400] designing the form to fire certain actions [412] when a user answers decision point [415, 414] questions in a certain way. This concept can be utilized for creating workflows, linking forms together, creating and updating queue items (aka tasks) (illustrated in and discussed with respect to, for example, FIG. 7), organizing data into cases (as illustrated in and discussed with respect to, for example, FIG. 1). Criteria [600] can be defined that determine whether or not an action fires. This allows the administrator to setup if/then statements based on the user's responses to various fields within a form. Combined with the tree-like structure of forms, extremely dynamic, admin-configured combinations of actions can be triggered from a form. Multiple different criteria can be combined to ensure that the conditions are met, or one of the conditions, before the action will be executed. Rules [603] can be applied to queue-based actions. These rules [603] are executed when certain conditions are met within a given queue item. For instance, a queue item, created via an action, can be setup to respond to the change of queue item status, so that a specified user can be notified. Timers [604] can be configured to perform certain system-tasks based on the length of time that a queue item sits with a certain status or priority. This is configured as a part of the add to queue [606] action type. The use of timers [604] allows the system to trigger rules to execute based on time, so that a user can be notified when a specified Task is overdue, for instance. Queue button settings [602] enables users to launch forms from a queue item, and provides details as to what should happen when this button clicked like status changes, initiating timers [604] and rules [603].

In FIG. 7, queue items [703, 714] represent tasks for a given user [700] to perform. Via actions [FIG. 6] attached to forms [410], queue's [702] are populated with queue items [703] given the configured platform experience. In turn, queue items [703] have configurable call-to-action buttons [707] associated with them. These buttons (aka queue actions) [707] can be configured to launch additional forms [709], send a user [100] to a page [311], send data [110] to an external system via an API, or do something as simple as marking a queue item [703] as "complete." Within the server architecture [FIG. 9], the platform processes these queue items [703] based on their configured scheduled actions [FIG. 6], e.g., now, +3 hours, -5 days from date, etc. Every user [700] within the platform has his/her individual queue [702]. This acts as a repository for tasks or queue items [703] assigned specifically to that user to be organized, viewed, and ultimately completed. Every group of users [712] within the platform has a group queue [712 to 714]. This allows for tasks to be assigned to not a single person, but a group of people. One distinction between an individual queue [713] and a group queue [714] is in the fact that any member of the group can complete a task within a group queue [714], whereas that individual user can only complete a task within an individual queue [713]. Group queues [714] often make use of the checkout button [706], which allows an individual user to checkout a task and claim it as their own. This prevents the scenario where more than one user within a group would perform a task, as once a task is checked out, other members of the group can no longer complete the specified task. Tasks, or queue items [703, 714], are individual items assigned to a queue. Queue items [703,714] are created via actions, which are triggered and executed during the processing of a completed form. Queue items [703, 714] show up in the task list until they are completed. The status of a queue item [703, 714] determines whether or not a task is completed or awaiting completion. Administrators configure queue item statuses, so that a truly customized workflow system, utilizing rules, timers, and queue actions (illustrated in and discussed with respect to, for example. FIG. 6) can be configured. Statuses determine whether or not a task is to be considered "completed" by the system. More than one "completed" status can be defined. Once a task has been updated to a "completed" status, it no longer shows up in the task list, unless filters are used to show "completed" tasks. Queue items [703, 714] can have priority levels [703], which can be ordered according to importance. Priorities are configured by administrators, and can be assigned weights, with lower weights assigned to the top of the task list, and heavier weights assigned to the bottom of the task list. The system-default high priority is used to promote queue items [703, 714] marked as high priority to the top of the task list [703]. Combined with timers, queue item priority levels [715] can be set to change after a pre-determined amount of time, thereby ensuring that tasks deemed time-sensitive by the administrator can be given proper attention and focus within the queue interface. One or more queue actions (buttons) can be configured to show up on a queue item (task) [703, 714]. The buttons can be configured to take the user to various destinations, such as a page, an external link, or a form [709]. Queue buttons can also be configured to update the status or priority of a queue item [703, 714]. Once clicked, the status of the queue item can be changed to a completed status. In this way, buttons are used to update queue items, and ultimately perform tasks within the use-case [239]. The only exception to this behavior is a button that is used to launch a form. The queue item status or priority is not updated until after the form that has been launched has been successfully completed. All other types of queue buttons update the associated queue item [703, 714] when they are initially clicked. This allows for a user to click a button to launch a form from within a task, start (but not finish) the form, and come back later to find that the task is still awaiting completion within the queue's task List.

In FIG. 14, these forms and workflows [1400] can be selected, copied, and replicated from one platform [1401] onto another platform [1404] or placed in the platform's pathway application community [1403]. The pathway application community [1403] enables for these pathways to be for browsing, promotion and sale to another platform user. The platform's e-commerce system [106] enables platform owners to create a product type that has attributes like name, date, price for a specific pathway and make it available within the community for purchase. Additionally, the cost of the arbitrary pathway can be split between the host and its owner [1403].

FIG. 15 illustrates an example method [1500] for performing asynchronous communication in accordance with an example implementation of the present disclosure. As shown in FIG. 15, data is received pertaining to a medical condition of a patient (Block [1502]). For example, the data may comprise a workflow associated with a patient. For instance, as described with respect to FIG. 2, the workflow may provide a customizable care and/or recovery program for a patient based upon the patient's medical condition. The data may also comprise data received through one or more forms [109]. For example, the data may comprise video data, and the video data, in some implementations, may be video data of a model (e.g., medical personnel, etc.) providing communication and/or performing an activity related to a medical condition of the patient.

The method [1500] also includes storing the data as a data structure in a memory (Block [1504]). In an implementation of the present disclosure, the data pertaining to the medical condition is stored in a memory of the server architecture as described below and shown in FIG. 9. The method [1500] also includes asynchronously transmitting the data to a client device upon receiving a request to access the data from the client device (Block [1506]). For example, the server architecture asynchronously transmits the data to a client device upon receiving a request to access the data. In an implementation, the client device comprises a patient client device associated with a patient. In another implementation, the client device comprises a healthcare provider client device.

The method may also include causing the presentation of a side-by-side video display, which is discussed above and shown in FIG. 8, at a patient client device (Block [1508]). As discussed above, the side-by-side video display includes a first video display area for displaying a video showing a model (e.g., medical personnel, etc.) presenting an activity to the patient. For example, the activity may be a rehabilitation activity, a post-operative follow-up activity, or the like. The side-by-side video display also includes a second video display area for displaying the video recorded of the patient performing the activity. This recorded data cart be stored as a data structure in the memory and asynchronously accessed by medical personnel to evaluate the patient's condition based upon the activity performed by the patient.

FIG. 9 depicts the underlying server (hardware) architecture that enables FIG. 1-FIG. 8, and any future additions to the platform. A request comes into the server architecture, through initial security [901] protocols (utilizing encryption, such as for example aes encryption, during transmission and non-transmission) and then to either a video server or device [903] or web server or device [902]. Video server(s) or device(s) [903] store the videos on temp storage server(s) or device(s) [904] until further processing, an example would be the recording process prior to the submission of an endpoint. Web server(s) or device(s) [902] receive all other requests and perform initial request routing as follows: A GET request for a previously uploaded file (stored on [906]) is processed by the web server(s) or device(s) [902] and then passed along to the filestore [906], which processes the request and returns the appropriate response to [902]. The web server(s) or device(s) [902] processes a GET request for a static resource and the resource is returned. The web server(s) or device(s) [902] passes along a GET request for a dynamic resource to the application server(s) or device(s) [905]. The application server(s) or device(s) [905] then process the GET request and return the dynamically generated resource. A POST request is processed dynamically, dependent on URL and contents. If a file is uploaded [908] as part of a POST request, the file type, file metadata and other data sent along in the POST request are used to dynamically process the file. The web server(s) or device(s) [902] pass along the request to the upload server(s) or device(s) [908]. The upload server(s) or device(s) [908] split the request up into parts. The first part that contains the file contents and file metadata are stored temporarily to temp storage server(s) or device(s) and then moved onto the storage server(s) or device(s). At the same time, the rest of the data in the POST request and the file metadata information is forwarded on to upload process server(s) or device(s) [909], which process the POST data to determine any action to be taken with the uploaded file. If there is any further processing to be done on the file, based on the file metadata and POSTed field data, the upload process server(s) or device(s) [908] will process the data, store relevant data in the datastore and set up a job or jobs [901] to be run against the file in the job server(s) or device(s) [910] to be completed separately from the request. At this point, the generated response is then sent back along the inverse path to the browser [907]. If a file is not uploaded as part of a POST request, the web server(s) or device(s) [902] pass along the request to the application server(s) or device(s) [905], which then process the POSTed data, storing it in the datastore [906] and generating the response which is returned to the browser along the inverse path. If the POSTed data includes references to a video recorded by the video server(s) or device(s) [903], the application server(s) or device(s) [905] can issue a request for the recorded file to be moved from temporary storage server(s) or device(s) [904] to the filestore server(s) or device(s) [906]. If any job(s) were generated as part of a request, the details of the job are held in the job server(s) or device(s) [910] until an available worker requests it's next job from the job server(s) or device(s) [910]. At this point, the worker [907] retrieves the details of the job from the job server(s) or device(s) [910] and begins processing. The worker server(s) or device(s) [907] will interact with the datastore [906] and filestore [906] as needed to get the information that it needs to do the job. After completion of the job, it will store the resulting data in the filestore [906] and datastore [906] as appropriate. The worker [907] will then go and request it's next job from the job server(s) or device(s) [910].

There are a variety of potential applications for the asynchronous video collaboration workflow engine described herein, such as for example the healthcare market, educational space, athletics, training and any other area that can benefit from asynchronous video collaboration and/or workflow. For illustration, we discuss an example application in the healthcare market and outline just a few use-cases that a health system would use the workflow management and asynchronous video collaboration platform for in their day-to-day use. Once the admin has created an experience, what unfolds and deploys within the organization can be any number of asynchronous collaborative experiences (use-cases) between one or more users. For example, in healthcare: patient-to-specialist post-operative follow-up and rehab: the disclosure's asynchronous, video-based remote follow-up visit process will provide the end-to-end experience for the patient. The platform's asynchronous collaboration process in this setting will enable surgeons to see the post-operative patient remotely. The patient, family member, or care giver (e.g., visiting nurse, physical therapist) can record a video (using any device, from anywhere, and at anytime) of the post-operative exam, utilizing the disclosure's interfaces for easy-to-follow along video routines (illustrated in and discussed with respect to, for example, FIG. 8). After the recording is submitted, the surgeon can review the video at anytime and provide video feedback (illustrated in and discussed with respect to, for example, FIG. 7), send orders, and coordinates further follow up. Also if there is an issue postoperatively, instead of the patient having to come to the office, the visit can be done remotely. This saves time and frustration for the patient and surgeon, while improving accessibility. It will also reduce unnecessary readmissions to the hospital. With follow-up visits in the post-operative setting typically being non-reimbursable due to the Affordable Care Acts bundled payment process, approximately 40% of specialist's work days will be spent doing uneventful visits, while the patient, in the end, would have rather completed these visits from home.

For the purpose of providing more precise workflow aspects related to post-operative follow-up utilizing the platform, the following provides an example step-by-step workflow.

The surgical coordinator logs into his or her account associated with the platform, goes to the dashboard and clicks on post-operative follow-up programs. The surgical coordinator arrives on a form where he or she selects a patient (potentially from an electronic medical record if integrated via an API), enters the patient's surgery date (which will trigger the follow-up tasks to provide based on the health system's standardized protocols for post-operative follow-up), and clicks submit.

Now that the surgical coordinator has initiated a post-operative follow-up program for a patient via the platform, the patient and/or partner-in-health (a person that helps the patient) receives a task notification via email, SMS text message or automated recorded phone call at the appropriate time in the future (e.g., approximately, two-weeks from the surgery date). The notification triggers the patient to login to his or her account and view his or her task. Once the patient logs into his or her account and goes to his or her dashboard, he or she will see an active task to complete. The patient clicks on the task, it opens and be or she sees a recorded video from his or her surgeon, explaining the post-operative follow-up task. The patient clicks continue and he or she sees a decision question, "Are you experiencing any pain?" The patient either chooses "yes" or "no." if the patient chooses "yes," then the resultant submission of a completed task will be assigned to his or her surgeon. If the patient chooses "no," then the resultant submission of the completed task will be assigned to the surgeon's group of physician assistants (discussed further below). If the patient chooses "no," the next screen the patient sees is the next step, which is the side-by-side video recording process. The patient clicks "record," and the left-side video begins to play and the right-side video begins to record. The left-side video provides instructions on the movements that he or she is supposed to complete. The patient mirrors the movements and the recording automatically completes itself because there is a time countdown on the right-side video. Now that the patient has completed his or her recording, he or she clicks "submit to my surgeon and his or her team."

Since the patient chose "no" to having any pain, the task is routed to the surgeon's physician assistants' group task list. The physician assistants all receive an optional notification to login and review the patient's recorded follow-up submission. All of the physician assistants login, but only one of the physician assistants check-out the task in order to review it and provide feedback and next step instructions. The physician assistant clicks on "provide feedback to patient" and arrives at a predetermined and standardized response form. The response form includes the ability for the physician assistant to append a pre-recorded video from the surgeon, record a video in real-time using the camera on his or her computer, tablet or smartphone, and/or add a pre-recorded response from him or her and append educational content to the response. The physician assistant uses a pre-recorded video from the surgeon that explains everything looks great and continue with rehab as prescribed. The physician assistant clicks send to patient.

The patient and his or her partner-in-health receive a notification that the specialist (surgeon) has responded to his or her submitted two-week follow-up recorded video. The patient logs in and sees the response task, views the physician's feedback and clicks marked viewed.

The results of this process are that the patient did not have to go to the office for an uneventful follow-up visit. The surgeon is able to open an in-person office visit that yields a reimbursable event versus seeing the uneventful follow-up visit which also a non-reimbursable event.

The process outlined above was configured by a platform admin using the workflow engine, which enables the admin to add the asynchronous video components into the process. This is one example of many that can be configured on the platform.

Another example is surgical coordination within the hospital setting: The coordination of the total joint replacement patient during the pre, peri, and post-operative periods is a challenging complex process. For example, it may involve at least twenty-five participants who need information concurrently in a timely basis. If there is a breakdown in communication between these participants, then patient care is compromised, patient satisfaction is poor, and/or cancellations or postponements of the surgery occur. For example: on average within the hospital setting, there is a 25% cancellation rate of total joint replacements due to failure of coordination of this patient population. In addition, hundreds of employee man-hours are wasted on inefficient processes to coordinate the care of these patients. Furthermore, there is no mechanism in place to track accountability of the many participants involved in this process. The disclosure's asynchronous telehealth platform can enable the coordination of pre-, peri-, and post-operative care of total joint patients. The platform automates care coordination processes. In this case, it can connect all 25 participants in the care of the total joint patient so everyone has the information that is needed, when it is needed. The platform also alerts participants if information is not present and holds each participant accountable to their specific tasks in the care of the patient.

Still another embodiment involves a computer-readable medium comprising processor-executable instructions configured to implement one or more of the techniques, platform and/or workflow presented herein. An exemplary computer-readable medium that may be devised in these ways is illustrated in FIG. 10, wherein the implementation [1000] comprises a computer-readable medium [1016] (e.g., a CD-R, DVD-R, or a platter of a hard disk drive), on which is encoded computer-readable data [1014]. This computer-readable data [1014] in turn comprises a set of computer instructions [1012] configured to operate according to one or more of the principles set forth herein. In one such embodiment [1000], the processor-executable computer instructions [1012] may be configured to perform a method [1010], such as at least some of the exemplary system/method 100 of FIG. 1, for example. In another such embodiment, the processor-executable instructions [1012] may be configured to implement a system, such as at least some of the exemplary system/method 200 of FIG. 2, for example. Many such computer-readable media may be devised by those of ordinary skill in the art that are configured to operate in accordance with the techniques presented herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

FIG. 11 and the following discussion provide a brief, general description of a suitable computing environment to implement embodiments of one or more of the provisions set forth herein. The operating environment of FIG. 11 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 11 illustrates an example of a system [1110] comprising a computing device [1112] configured to implement one or more embodiments provided herein. In one configuration, computing device [1112] includes at least one processing unit [1116] and memory [1118]. Depending on the exact configuration and type of computing device, memory [1118] may be volatile (such as RAM, for example), non-volatile (such as ROM, flash memory, etc., for example) or some combination of the two. This configuration is illustrated in FIG. 11 by dashed line [1114].

In other embodiments, device [1112] may include additional features and/or functionality. For example, device [1112] may also include additional storage (e.g., removable and/or non-removable) including, but not limited to, magnetic storage, optical storage, and the like. Such additional storage is illustrated in FIG. 11 by storage [1120]. In one embodiment, computer readable instructions to implement one or more embodiments provided herein may be in storage [1120]. Storage [1120] may also store other computer readable instructions to implement an operating system, an application program, and the like. Computer readable instructions may be loaded in memory [1118] for execution by processing unit [1116], for example.

The term "computer readable media" as used herein includes computer storage media. Computer storage media includes volatile and nonvolatile, removable and non-removable media implemented in any method or technology for storage of information such as computer readable instructions or other data. Memory [1118] and storage [1120] are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device [1112]. Any such computer storage media may be part of device [1112].

Device [1112] may also include communication connection(s) [1126] that allows device [1112] to communicate with other devices. Communication connection(s) [1126] may include, but is not limited to, a modem, a Network Interface Card (NIC), an integrated network interface, a radio frequency transmitter/receiver, an infrared port, a USB connection, or other interfaces for connecting computing device [1112] to other computing devices. Communication connection(s) [1126] may include a wired connection or a wireless connection. Communication connection(s) [1126] may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device [1112] may include input device(s) [1124] such as keyboard, mouse, pen, voice input device, touch input device, infrared cameras, video input devices, and/or any other input device. Output device(s) [1122] such as one or more displays, speakers, printers, and/or any other output device may also be included in device [1112]. Input device(s) [1124] and output device(s) [1122] may be connected to device [1112] via a wired connection, wireless connection, or any combination thereof. In one embodiment, an input device or an output device from another computing device may be used as input device(s) [1124] or output device(s) [1122] for computing device [1112].

Components of computing device [1112] may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device [1112] may be interconnected by a network. For example, memory [1118] may be comprised of multiple physical memory units located in different physical locations interconnected by a network.

Those skilled in the art will realize that storage devices utilized to store computer readable instructions may be distributed across a network. For example, a computing device [1130] accessible via a network [1128] may store computer readable instructions to implement one or more embodiments provided herein. Computing device [1112] may access computing device [1130] and download a part or all of the computer readable instructions for execution. Alternatively, computing device [1112] may download pieces of the computer readable instructions, as needed, or some instructions may be executed at computing device [1112] and some at computing device [1130]. In some implementations of the present disclosure, the computing device [1112] comprises a server computing device for providing asynchronous communication functionality as described above, and the computing device [1130] comprises a client device. For example, the computing device [1130] may comprise a client device associated with a patient or a client device associated with a healthcare service provider. While only one computing device [1112] and computing device [1130] is shown in FIG. 11, it is understood that the system [1110] may include multiple computing devices [1112] and computing devices [1130] without departing from the spirit of the present disclosure.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

Moreover, the word "exemplary" is used herein to mean serving as an example, instance, or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B and/or the like generally means A or B or both A and B.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

Having described at least one of the example embodiments of the present disclosure with reference to the accompanying drawings, it is to be understood that the disclosure is not limited to those precise embodiments, and that various changes, modifications, and adaptations may be effected therein by one skilled in the art without departing from the scope or spirit of the disclosure as defined in the appended claims.

What is claimed is:

1. A system for performing asynchronous communication within a healthcare system, comprising:
   a patient client device including a processor and a memory with program instructions executable by the processor, wherein the program instructions cause the processor to:
      present a side-by-side or picture-in-picture video display based on video data pertaining to a medical condition of a patient, the side-by-side or picture-in-picture video display including a first video display area and a second video display area, the first video display area including a video of a model presenting an activity to the patient, the second video display area configured to present a real-time or near real-time video stream of the patient to the patient while recording a video of the patient performing the activity;
      in response to receiving a selection at the patient client device to record the video of the patient performing the activity, simultaneously present, via the side-by-side or picture-in-picture video display, the video of the model presenting the activity to the patient and the real-time or near real-time video stream of the patient performing the activity; and
      transmit the recorded video data including the recorded video of the patient performing the activity to a video server, wherein a storage server is in communication with the video server and configured to store the recorded video data after the recorded video data is processed by the video server, and wherein a web server is in communication with the storage server and configured to receive a request from a healthcare provider client device to access the recorded video data and further configured to retrieve the recorded video data from the storage server and asynchronously transmit the recorded video data to the healthcare provided client device,
   wherein the video server is further configured to receive data from the healthcare provider client device, the data including the video data pertaining to the medical condition of the patient,
   wherein the storage server is further configured to store the data including the video data pertaining to the medical condition of the patient, and
   wherein the web server is further configured to receive a request from the patient client device to access the data including the video data pertaining to the medical condition of the patient, retrieve the data including the video data pertaining to the medical condition of the patient from the storage server, and asynchronously transmit the data including the video data pertaining to the medical condition of the patient to the patient client device after receiving the request to access the data from the patient client device.

2. The system of claim 1, wherein a temporary storage server is in communication with the video server and the storage server, and the temporary storage server is configured to store an unprocessed or partially processed version of the data including the video data pertaining to the medical condition of the patient before the data is transmitted to the storage server.

3. The system of claim 1, wherein an application server is in communication with the web server, and the application server is configured to receive the request from the patient client device when the request is for a dynamic resource.

4. The system of claim 1, wherein an upload server is in communication with the web server, and the upload server is configured to receive the request from the patient client device when the request includes a file to be uploaded.

5. The system of claim 4, wherein an upload process server is in communication with the upload server, and the upload process server is configured to receive metadata associated with the file and to determine one or more actions to be taken based on the metadata.

6. The system of claim 5, wherein a job server is in communication with the upload process server, and the job server is configured to receive details for one or more jobs based on the one or more actions determined by the upload process server.

7. The system of claim 6, wherein a worker server is in communication with the job server, and the worker server is configured to request a job from the job server, receive details for the job in response to the request, and execute the job.

8. The system of claim 1, wherein the patient client device is configured to present the video including the model presenting the activity to the patient before permitting video recording of the patient performing the activity.

9. A system for performing asynchronous communication within a healthcare system, comprising:
   one or more servers including one or more processors and memory with program instructions executable by the one or more processors, the one or more servers being configured to:

receive data from a healthcare provider client device, the data including video data pertaining to a medical condition of a patient;

store the data including the video data pertaining to the medical condition of the patient;

receive a request from a patient client device to access the data including the video data pertaining to the medical condition of the patient; and retrieve the data including the video data pertaining to the medical condition of the patient and asynchronously transmit the data including the video data pertaining to the medical condition of the patient to the patient client device after receiving the request to access the data from the patient client device, wherein the patient client device includes a processor and memory with program instructions executable by the processor, and the patient client device is configured to:

present a side-by-side or picture-in-picture video display based on the video data pertaining to the medical condition of the patient, the side-by-side or picture-in-picture video display including a first video display area and a second video display area, the first video display area including a video of a model presenting an activity to the patient, the second video display area configured to present a real-time or near real-time video stream of the patient to the patient while recording a video of the patient performing the activity; and in response to receiving a selection at the patient client device to record the video of the patient performing the activity, simultaneously present, via the side-by-side or picture-in-picture video display, the video of the model presenting the activity to the patient and the real-time or near real-time video stream of the patient performing the activity, wherein the one or more servers are further configured to receive recorded video data including the recorded video of the patient performing the activity, store the recorded video data after the recorded video data is processed, receive a request from the healthcare provider client device to access the recorded video data, and retrieve the recorded video data and asynchronously transmit the recorded video data to the healthcare provided client device.

10. The system of claim 9, further comprising:
a temporary storage server in communication with the one or more servers, the temporary storage server being configured to store an unprocessed or partially processed version of the data including the video data pertaining to the medical condition of the patient before the data is transmitted to the one or more servers.

11. The system of claim 9, further comprising:
an application server in communication with the one or more servers, the application server being configured to receive the request from the patient client device when the request is for a dynamic resource.

12. The system of claim 9, further comprising:
an upload server in communication with the one or more servers, the upload server being configured to receive the request from the patient client device when the request includes a file to be uploaded.

13. The system of claim 12, further comprising:
an upload process server in communication with the upload server, the upload process server being configured to receive metadata associated with the file and to determine one or more actions to be taken based on the metadata.

14. The system of claim 13, further comprising:
a job server in communication with the upload process server, the job server being configured to receive details for one or more jobs based on the one or more actions determined by the upload process server.

15. The system of claim 14, further comprising:
a worker server in communication with the job server, the worker server being configured to request a job from the job server, receive details for the job in response to the request, and execute the job.

16. The system of claim 9, wherein patient client device is configured to present the video including the model presenting the activity to the patient before permitting video recording of the patient performing the activity.

\* \* \* \* \*